(12) United States Patent
Candy et al.

(10) Patent No.: US 8,584,506 B2
(45) Date of Patent: Nov. 19, 2013

(54) PHYSICS-BASED SIGNAL PROCESSING ALGORITHMS FOR MICROMACHINED CANTILEVER ARRAYS

(75) Inventors: James V. Candy, Danville, CA (US);
David S. Clague, Livermore, CA (US);
Christopher L. Lee, Oakland, CA (US);
Robert E. Rudd, Livermore, CA (US);
Alan K. Burnham, Livermore, CA (US); Joseph W. Tringe, Walnut Creek, CA (US)

(73) Assignee: lawrence Livermore National Security, LLC., Livermore, CA (US)

( * ) Notice: Subject to any disclaimer, the term of this patent is extended or adjusted under 35 U.S.C. 154(b) by 1456 days.

(21) Appl. No.: 11/435,495

(22) Filed: May 16, 2006

(65) Prior Publication Data
US 2007/0093971 A1    Apr. 26, 2007

Related U.S. Application Data

(60) Provisional application No. 60/683,121, filed on May 17, 2005.

(51) Int. Cl.
G01N 9/00      (2006.01)
G01N 31/00     (2006.01)

(52) U.S. Cl.
USPC .............................. 73/23.21; 702/27; 702/32

(58) Field of Classification Search
USPC ........ 73/19.01, 23.21, 23.2; 422/50, 68.1, 69, 422/83, 88; 702/27, 32
See application file for complete search history.

(56) References Cited

U.S. PATENT DOCUMENTS

| | | | |
|---|---|---|---|
| 5,908,981 A | 6/1999 | Atalar et al. | |
| 6,237,399 B1 | 5/2001 | Shivaram et al. | |
| 6,606,567 B2 | 8/2003 | Grate et al. | |
| 2002/0094531 A1 | 7/2002 | Zenhausern | |
| 2004/0120577 A1 | 6/2004 | Touzov | |
| 2004/0256552 A1 | 12/2004 | Kawakatsu | |
| 2006/0016270 A1 | 1/2006 | Cavenago et al. | |
| 2006/0070451 A1 | 4/2006 | Walsh et al. | |
| 2006/0075836 A1 | 4/2006 | Zribi et al. | |

OTHER PUBLICATIONS

T.A. Betts et al., Selectivity of Chemical Sensors Based on Micro-Cantilevers Coated With Thin Polymer Films, 422 ANAL. CHIM. ACTA 89-99 (2000).*
R. Marie et al., Adsorption Kinetics and Mechanical Properties of Thiol-Modified DNA-Oligos on Gold Investigated by Microcantilever Sensors, 91 Ultramicroscopy 29-36 (2002).*
J.W. Tringe et al., Model-Based Processing of Microcantilever Sensor Arrays, Lawrence Livermore National Laboratory (Nov. 23, 2004).*
D.W. Dareing and T. Thundat, Simulation of Adsorption-Induced Stress of a Microcantilever Sensor, 97 J. Appl. Phys. 043526 (2005).*
Paddle, Brian M., "Biosensors for chemical and biological agents of defence interest," Biosensors & Bioelectronics vol. 11, No. 11, pp. 1079-1113, 1996.
Raiteri, R., et al., "Micromechanical cantilever-based biosensors," Sensors and Actuators B, 79, (2001) , pp. 115-126.
Rennie, G., "Measuring Contact Stress Inside Weapon Systems," Lawrence Livermore National Laboratory, Science & Technology Review, Apr. 2006, 6 pages.
Tringe, J. W., et al., "Model-based Processing of Microcantilever Sensor Arrays," Lawrence Livermore National Laboratory, Nov. 23, 2004, pp. 1-24.
Tringe, Joseph W., Model-Based Processing of Microcantilever Sensor Arrays, Journal of Microeletrochemical Systems, vol. 15, No. 5.

* cited by examiner

*Primary Examiner* — Randy Boyer
(74) *Attorney, Agent, or Firm* — Eddie E. Scott

(57) ABSTRACT

A method of using physics-based signal processing algorithms for micromachined cantilever arrays. The methods utilize deflection of a micromachined cantilever that represents the chemical, biological, or physical element being detected. One embodiment of the method comprises the steps of modeling the deflection of the micromachined cantilever producing a deflection model, sensing the deflection of the micromachined cantilever and producing a signal representing the deflection, and comparing the signal representing the deflection with the deflection model.

1 Claim, 15 Drawing Sheets

PHYSICS-BASED SIGNAL PROCESSING ALGORITHMS FOR MICROMACHINED CANTILEVER ARRAYS

CROSS-REFERENCE TO RELATED APPLICATIONS

This application claims the benefit of U.S. Provisional Patent Application No. 60/683,121 filed May 17, 2005 and titled "Physics-Based Signal Processing Algorithm for Micromachined Cantilever Arrays." U.S. Provisional Patent Application No. 60/683,121 filed May 17, 2005 and titled "Physics-Based Signal Processing Algorithm for Micromachined Cantilever Arrays" is incorporated herein by this reference.

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to micromachined cantilevers and more particularly to physics-based signal processing algorithm for micromachined cantilever arrays.

2. State of Technology

U.S. Pat. No. 5,908,981 issued Jun. 1, 1999 to Abdullah Atalar et al and assigned to the Board of Trustees of the Leland Stanford, Jr. University provides the following state of technology information, "a microcantilever includes a pattern of interdigitated fingers that together form a phase grating. The phase grating is used to sense deflection of the microcantilever. In the pattern, movable fingers alternate with reference fingers. The movable fingers are physically connected to the tip of the microcantilever and move with the cantilever as it deflects; the reference fingers are physically connected to the fixed end of the cantilever and do not move as the cantilever deflects. Each reference finger is bounded on either side by movable fingers, and each movable finger is bounded on either side by a reference finger (ignoring the fingers at the ends of the pattern)."

U.S. Patent Application No. 2004/0120577 by Igor Touzov published Jun. 24, 2004 provides the following state of technology information, "Development of diverse set of applications that employs micro and nano scale properties of matter created equally wide range of equipment that is able to operate at such small scales. One of primary advantages of such technologies is the ability to efficiently and cheaply employ parallel processing for large number of entities. These parallel technologies have been developed for processing of thousands and even millions of chemicals on a single microfluidic/microarray device. Microoptical devices accounts several millions of parallel processing channels suitable for diverse tasks such as maskless lithography, printing, network switching, etc. Micromechanical and micro-electro mechanicals systems are capable of simultaneous execution of thousands and sometimes millions of simultaneous mechanical operations required for microfluidics, microoptics and micromachining."

The article "Micromechanical Cantilever-based Biosensors" by Roberto Raiteri, Massimo Grattarola, Hans-Jürgen Butt, and Petr Skládal in *Sensors and Actuators B:Chemical*, Volume 79, Issues 2-3, Oct. 15, 2001, pages 115-126 provides the following state of technology information, "Microcantilevers can transduce a chemical signal into a mechanical motion with high sensitivity." Generally, biosensing is a more demanding task than physical or chemical sensing because of the complexity of the biochemical processes involved and the nature of the operation environment. Biosensors have attracted considerable interest in the last few years since the monitoring of a specific substance is central in many applications ranging from clinical analysis to environmental control and for monitoring many industrial processes. A biosensor, as any other sensing device, can be divided into three main components: a detector which recognizes the signal of interest, a transducer which converts the signal into a more useful output, typically an electronic signal, and a read-out system which filters, amplifies, displays, records, or transmits the transduced signal. A biosensor employs a biological or biochemical detector, which can range from single proteins and enzymes up to whole cells and microorganisms. In biosensing applications, detection is usually carried out in a liquid (aqueous) environment. Flow and mixing of the solution cause turbulence which directly affects cantilever deflection. Additional drifts in deflection have been observed. They can be due to both slow electrochemical processes on either side of the cantilever and to rearrangements of the sensing surface, which is usually composed by multilayers of complex molecules like proteins.

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

Micromachined cantilevers can sense chemicals and biological molecules of interest for biodefense and pollution-control applications. Microcantilevers function in liquid and in air environments, and they are inexpensive because they are batch fabricated in large numbers using techniques similar to those used to make microelectronic circuits. It is often difficult to extract meaningful signals from the cantilevers; however, due to the sensitivity of these devices to a wide variety of stimuli.

The present invention provides methods of detecting a parameters utilizing deflection of a micromachined cantilever. The methods utilize deflection of a micromachined cantilever that represents the particular parameter being detected. Embodiments of the present invention provide methods of detecting chemical and biological agents utilizing micromachined cantilevers. One embodiment of the method comprises the steps of modeling the deflection of the micromachined cantilever producing a deflection model, sensing the deflection of the micromachined cantilever and producing a signal representing the deflection, and comparing the signal representing the deflection with the deflection model. In another embodiment, the present invention includes a physics-based signal extraction algorithm that makes used of thermodynamic, fluidic and mechanical properties of a micromachined cantilever array and its environment in order to maximize signal to noise ratios. For micromachined cantilever-based sensors, large, nonspecific background signals prevent deflections caused by target chemicals and biological molecules from being identified.

The present invention enables detection of chemicals and biological molecules of interest. The present invention can be used for environmental control, biodefense, and nonproliferation. The present invention can also be used for drug discovery, detection of pollutants, and chemical monitoring in fabrication processes. The present invention can also be used for can any system (e.g., making smart sensors that use the underlying physics).

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
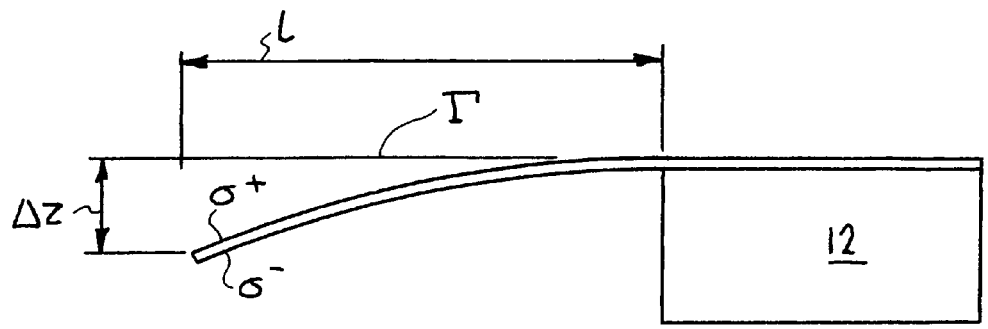
FIG. 1 shows a schematic side view of a micro-machined cantilever system.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Micromachined cantilevers are powerful transducers for sensing inorganic, organic and biological molecules, since they readily deflect in the presence of a very small number of target molecules (nanomolar to femtomolar concentrations). The number of potential target chemicals is large, ranging from DNA to explosives, suggesting that cantilevers may be useful in defense, medicine, drug discovery, and environmental monitoring. Microcantilevers have already been demonstrated to be capable of recognizing antibodies and nerve agent products such as hydrofluoric acid in solution, for example. Other cantilever-based sensors that have been developed perform other functions.

Referring now to the drawings and in particular to FIG. 1, a schematic side view of a micro-machined cantilever system is shown. The system is designated generally by the reference numeral 10. The micro-machined cantilever 11 extends from a body 12. FIG. 1 shows cantilever length, l, deflection, $\Delta z$, surface stress, $\sigma+$ and $\sigma-$, and surface concentration of target species. Adsorption of the target species on the top cantilever surface induces a measurable deflection of the cantilever 11.

A limitation on cantilever sensors in liquid, however, is that their signal-to-noise ratio (SNR) is low, often 5:1 or smaller. SNR is expected to be significantly lower in many operational environments of interest. Further, the reliability of fielded cantilever sensors ultimately depends on their being incorporated into arrays, which increase system complexity and can make response interpretation difficult. Fortunately, these difficulties are exactly the type that can be overcome with effective signal extraction techniques such as the present invention model-based approach. The present invention takes advantage of multiple redundant signals available to the signal processing algorithm. This approach improves the SNR and helps provide a physical basis for interpreting the deflection signal.

The micromachined cantilever system 10 can function as a detection device when one side is fabricated to be chemically distinct from the other, as illustrated in FIG. 1. Functionalization can be accomplished, for example, by evaporating a thin (~10's of nm) film of metal such as Au on the top of the chip, then immersing the cantilever chip in a "probe" chemical that will bind preferentially to the Au thin film. The lever acts as a sensor when it is exposed to a second "target" chemical that reacts with the probe, since the reaction causes a free energy change that induces stress at the cantilever surface. Differential surface stress, $\Delta\sigma(=\Delta\sigma^+ - \Delta\sigma^-)$, from FIG. 1, in turn, induces a deflection of the cantilever that can be measured optically or electronically. Results of experiments with Au-coated cantilevers exposed to 2-mercaptoethanol ($C_2H_6OS$), a small sulfur-terminated molecule with high affinity for Au, will be described. It is noted that the signal-processing approach developed here should apply well to cantilevers that are functionalized to promote the binding of other chemicals or biological molecules.

The micromachined cantilever system 10 can be used for detecting chemical and biological agents. Examples of the use of the micromachined cantilever system 10 range from clinical analysis to environmental control and for monitoring many industrial processes. The micromachined cantilever system 10 can also be used for detecting chemical and biological agents of defense interest. The article "Micromechanical Cantilever-based Biosensors" by Roberto Raiteri, Massimo Grattarola, Hans-Jürgen Butt, and Petr Skládal in *Sensors and Actuators B:Chemical*, Volume 79, Issues 2-3, Oct. 15, 2001, pages 115-126 describes uses of the micromachined cantilever system 10. The article "Micromechanical Cantilever-based Biosensors" by Roberto Raiteri, Massimo Grattarola, Hans-Jürgen Butt, and Petr Skládal in *Sensors and Actuators B:Chemical*, Volume 79, Issues 2-3, Oct. 15, 2001, pages 115-126 is incorporated herein by reference. Other uses of the micromachined cantilever system 10 are described in the article, "Biosensors for Chemical and Biological Agents of Defence Interest," by Brian M. Paddle in *Biosensors & Bioelectronics*, Vol. 11, No. 11, pp. 1079-1113, Feb. 13, 1996. The article "Biosensors for Chemical and Biological Agents of Defence Interest," by Brian M. Paddle in *Biosensors & Bioelectronics*, Vol. 11, No. 11, pp. 1079-1113, Feb. 13, 1996 is incorporated herein by reference.

The total free energy change of the cantilever surface, $\Delta G$, can be decomposed into four contributions: $\Delta G_{CANT}$, the mechanical energy change associated with bending the cantilever, $\Delta G_{POLY}$, free energy change resulting from macromolecular conformational entropy and non-electrostatic interactions, $\Delta G_{OSM}$, free energy change from osmotic pressure of counter-ions near the surface of the cantilever, and $\Delta G_{ELEC}$, the electrostatic free energy change.

$$\Delta G = \Delta G_{CANT} + \Delta G_{POLY} + \Delta G_{OSM} + \Delta G_{ELEC} \quad \text{(Equation 1)}$$

The free energy change is related to $\Delta \sigma$, the surface stress difference between top and bottom side of the cantilever by:

$$\Delta \sigma(t) = \Delta G(t) \Gamma(t) / M_A \quad \text{(Equation 2)}$$

where $\Delta G$ has units of J/mole and is the change in the sum of all of the contributions to the free energy of the surface of the cantilever, $\Gamma(t)$ is the surface concentration of the species of interest (typically in molecules per cm²) on the surface of the cantilever and $M_A$ is Avogadro's number. Sulfur-terminated molecules bind preferentially to the Au-coated side of the cantilever.

The surface concentration of the interacting molecules, $\Gamma(t)$, is estimated using Langmuir kinetics. The equation describing first-order Langmuir kinetics has the following form:

$$\frac{d\left(\frac{\Gamma(t)}{\Gamma_{max}}\right)}{dt} = k_a c(t)\left(1 - \frac{\Gamma(t)}{\Gamma_{max}}\right) - k'_d \Gamma(t) \quad \text{(Equation 3)}$$

Here $c(t)$ is the bulk concentration of the target molecule in solution in moles per liter, or [M], $k_a$ is the adsorption rate constant in [M]$^{-1}$ s$^{-1}$, $k_d'$ ($=k_d/\Gamma_{max}$) is the desorption rate constant in cm² molecule$^{-1}$ s$^{-1}$. $\Gamma_{max}$ is the maximum possible surface concentration of the species of interest in molecules cm$^{-2}$, which is approached asymptotically at equilibrium as the solution concentration becomes very large. Finally, differential surface stress, from (2), in the cantilever induces a deflection, $\Delta z(t)$, using a variant of Stoney's equation:

$$\Delta z(t) = \frac{3l^2(1-v)}{E\delta^2} \Delta \sigma(t), \quad \text{(Equation 4)}$$

where E is the Young's modulus, v is the Poisson's ratio, and l and $\delta$ are the cantilever length and thickness, respectively.

The terms multiplying the differential surface stress are system-specific constants and can be combined and expressed as a single coefficient, $$\Delta z(t) = \beta \Delta \sigma(t) \quad \text{(Equation 5)}$$

$$\text{Here, } \beta = 3l^2(1-v)/(E\delta^2). \quad \text{(Equation 6)}$$

The proportionality constant that relates cantilever deflection, $\Delta z(t)$, to induced surface stress due to surface coverage, $\Delta \sigma(t)$, can be written equivalently in terms of the spring constant of the rectangular cantilever, $k_{rect} = E\delta^3 W/(4l^3)$:

$$\Delta z_i^c(t) = \frac{3(1-v)}{4} \frac{W\delta}{l} \frac{1}{k_{rect}} \Delta \sigma_i(t) \quad \text{(Equation 7)}$$

where W is the width of the cantilever and the superscript c on $\Delta z$ indicates deflection from cantilever coverage by chemicals, as opposed to deflection from thermal effects. Correspondingly, the coefficient to the surface stress, $\beta$, given above can be rewritten as, $$\beta = \frac{3(1-v)W\delta}{4l k_{rect}}. \quad \text{(Equation 8)}$$

The equations describing the cantilever deflection (4-8) assume that the strain is small, an assumption that is valid for all of the deflections encountered in Applicants' experiments.

Applicants will now describe the prediction of changes in surface stress as a function of surface loading. The analysis also begins with Stoney's equation (4), which states that the deflection of the cantilever is directly proportional to the difference in surface stress on the cantilever surface. This stress differential constitutes the signal. Applicants follow the approach as described by Lavrik et al. to relate the surface stress difference to the surface coverage and the free energy of adsorption (2). What remains is to develop physical models for $\Gamma(t)$ and $\Delta G$.

When incorporating the rate of change of the dimensionless surface concentration, $\Gamma(t)/\Gamma_{max}$, for the MBP, Applicants employ a modified form of (3) by re-defining a rate of desorption, $k_d$, where $k_d = k'_d \Gamma_{max}$ and has units of s$^{-1}$. With this new definition (3) becomes:

$$\frac{d\left(\frac{\Gamma(t)}{\Gamma_{max}}\right)}{dt} = k_a c(t)\left(1 - \frac{\Gamma(t)}{\Gamma_{max}}\right) - k_d \frac{\Gamma(t)}{\Gamma_{max}} \quad \text{(Equation 9)}$$

All terms are as described above in (3) with the exception of $k_d$. This form, (9), was chosen to enable a one-to-one comparison between rate constants predicted by the MBP presented here.

Once the input signal, a bulk concentration $c_0$ of target molecules, is turned off, Applicants fit the desorption process with an $n^{th}$ order Langmuir desorption model:

$$\frac{d\left(\frac{\Gamma_i(t)}{\Gamma_{max}}\right)}{dt} = -k_d\left(\frac{\Gamma_i(t)}{\Gamma_{max}}\right)^n \quad \text{(Equation 10)}$$

The fit to the actual desorption data revealed a third-order dependence on the surface concentration, or n=3. Desorption processes are typically modeled with a first or second order model to extract $k_d$, and the preference for a third order model is somewhat surprising. The higher order behavior could indicate a cooperative desorption process, but it is more likely due to a distribution of activation energies associated with the desorption process.

Also included in the model-based processor is the cantilever response to thermal effects, deflections due to differences in the coefficient of thermal expansion of Au and Si. Thermally-induced deflections are added directly to chemically-induced deflections to obtain the total cantilever deflection. From, $$\Delta z^T = 3\Delta\alpha l^2 \frac{\delta_{Au} + \delta_{Si}}{\delta_{Si}^2 k_1} \Delta T \quad \text{(Equation 11)}$$

where $\Delta Z^T$ is the normal (z-direction) deflection of the free end of the cantilever, $\Delta T$ is the temperature difference, $\Delta\alpha$ is the difference in thermal expansion coefficients ($\alpha_{Si} - \alpha_{Au}$), l is the cantilever length, and $\delta$ is the thickness of the Si or Au. The superscript T on $\Delta z$ in Equation (11) indicates deflection from thermal effects, as opposed to chemical surface coverage which was previously indicated in Equation (7) by superscript c. The coefficient $k_1$ is given by $$k_1 = 4 + 6\frac{\delta_{Au}}{\delta_{Si}} + 4\left(\frac{\delta_{Au}}{\delta_{Si}}\right)^2 + \quad \text{(Equation 12)}$$
$$\frac{E_{Au}}{E_{Si}}\frac{(1-v_{Si})}{(1-v_{Au})}\left(\frac{\delta_{Au}}{\delta_{Si}}\right)^3 + \frac{E_{Si}}{E_{Au}}\frac{(1-v_{Au})}{(1-v_{Si})}\left(\frac{\delta_{Si}}{\delta_{Au}}\right)$$

Here E is Young's modulus for Si or Au, and v is Poisson's ratio for Si or Au. Note the Poisson effect has been included in $k_1$, and that the gold layer is relatively thin so the final term dominates the expression for $k_1$.

The models describing the physics of the cantilever bending and the surface chemistry were built into the model-based signal processor, and a parameter estimator was developed to fit these coupled equations predicting the optimal values for $k_a$, $k_d$ and $\Gamma_{max}$. With these parameters specified, Applicants calculate the free energy for adsorption, adsorption $$\Delta G_{ads} = -RT\ln\left(\frac{k_a}{k_d}\right).$$

For any target species, Applicants can then fit to find the appropriate adsorption parameters.

A prototype cantilever detection system from Veeco Instruments, Inc., was used for Applicants' experiments. In this system, a single Si chip (fabricated by IBM) with eight identical cantilevers is loaded into a 50 microliter flow cell, and cantilever deflections are measured optically using a focused light beam from a super-luminescent diode reflected into a position-sensitive detector by each cantilever. Levers are interrogated in series, with an overall measurement frequency of ~2 Hz for all eight levers. Each Si cantilever is 500 microns long, 100 microns wide and 1 micron thick; levers are parallel to one another on the chip, spaced by 100 microns. The top side of the levers (as depicted in FIG. 1) was coated with 20 nm of evaporated Au on a 2.5 nm Ti adhesion layer, and the whole chip was cleaned with piranha solution (3:1 $H_2SO_4$: 30% $H_2O_2$) immediately before being loaded into a water-filled 50 microliter flow cell.

Figure 2:
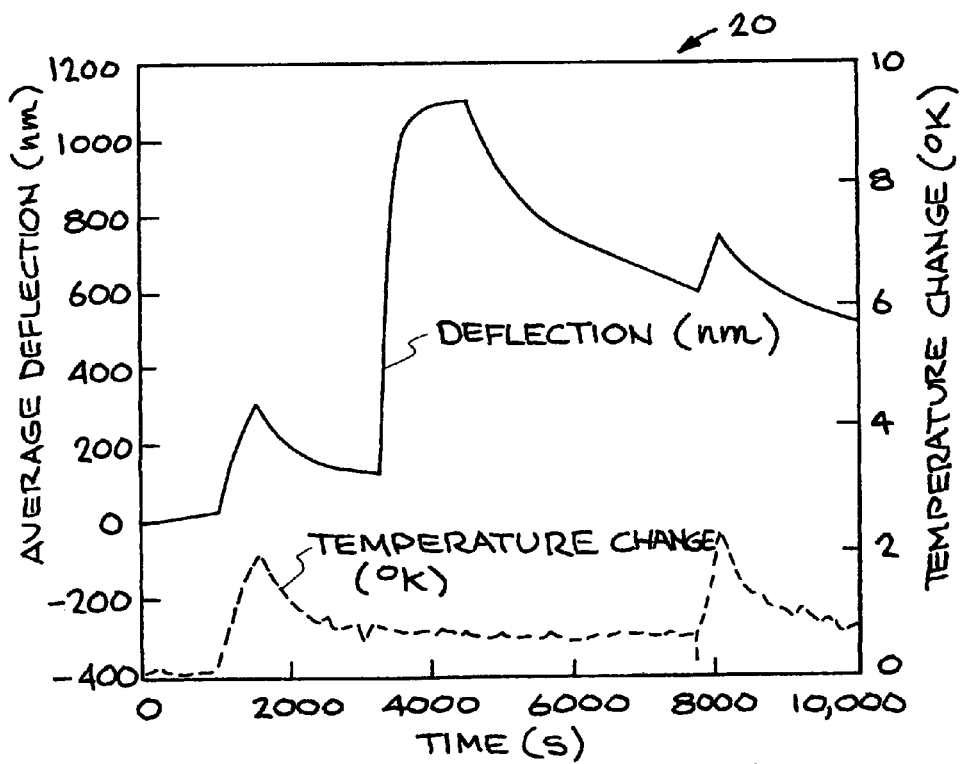
FIG. 2 is a graph wherein mean experimentally-measured deflection of the cantilevers due to temperature and chemical stimuli; deflection signal, averaged over six cantilevers, is shown by the dark solid line, individual cantilever deflections are shown by light dashed lines, and the temperature change (dark dashed line) was measured in the fluid exiting the cell.

During the experiment, levers were exposed to a thermal pulse, then a chemical stimulus in the form of a $c_0$=0.014 M concentration of 2-mercaptoethanol in pure water, and finally a second heat pulse. Except for brief pauses to exchange syringes in the syringe pump, the entire experiment was performed at a constant flow rate of 20 microliter/min. Results of this experiment are shown in FIG. 2: the average deflection of 6 of 8 cantilevers (2 others were damaged), and simultaneous temperature measurements from a thermocouple placed in the flow of fluid exiting the cell. Similar experiments were repeated several times, and the data shown are typical of the magnitude and time evolution of the deflection and temperature signals.

Design for cantilever arrays—Applicants will describe the development of the model-based approach, first for the generic model sets and then for the specific embellishment discussed previously. Applicants start with the development of an approximate Gauss-Markov model, which can be used to capture the general cantilever signal enhancement problem. Applicants then apply it to Applicants specific microcantilever array sensor system. The scope of this section on model development involves specification of the process and measurement models for the cantilever system, construction of the model-based processor algorithm, estimation of the model parameters, verification of model performance on simulated data and validation of the model with real data. The testing with real experiments involves both single channel and multi-channel data.

If nonlinear dynamics (differential equations) describe the system under investigation, then an approximate representation of the deterministic process and associated measurement is easily captured in state-space form. State-space is simply converting an $n^{th}$-order set of coupled differential equations into an equivalent set of n first-order differential equations. With this accomplished, Applicants obtain the general non-linear vector functional relations defined by the process and measurement models, $\dot{x}(t)=a[x,u;\theta]$ [process (state)]

$y(t)=c[x,u;\theta]$ [measurement]  (Equation 13)

where x is the $N_x$-dimensional state vector; y is the $N_y$-dimensional measurement. u is a known input, and $\theta$ is a generic model parameter. If these processes are contaminated by additive zero-mean, Gaussian noise, then the approximate Gauss-Markov model evolves as $\dot{x}(t)=a[x,u;\theta]+w(t)$ [process (state)]

$y(t)=c[x,u;\theta]+v(t)$ [measurement]  (Equation 14)

Here a[.], c[.] are the $N_x$-dimensional vector process function and $N_y$-dimensional measurement functions, respectively, for the process noise given by $w \sim N(0,R_{ww})$ and the corresponding measurement noise, $v \sim N(0,R_{vv}) \cdot N(\cdot,\cdot)$ is the Gaussian distribution specified by mean and covariance. With this representation in mind, Applicants can now define the generic cantilever signal enhancement problem as:

Given a set of noisy displacement measurements, $\{y(t)\}$, with known inputs, $\{u(t)\}$, and parameters, $\{\theta\}$, specified by the approximate Gauss-Markov model of (14), FIND the best (minimum error variance) estimate of the displacement, $\hat{y}(t)$, and surface concentrations, $\hat{i}(t)$.

The solution to this problem can be derived in a wide variety of approaches. Here, Applicants will use the common Bayesian approach. Applicants summarize the algorithm as:

Model-Based Processor Algorithm $\hat{x}(t|t-1)=a[\hat{x},u;\theta]$ [State Prediction]

$\hat{y}(t|t-1)=c[\hat{x},u;\theta]$ [Measurement Prediction]

$\epsilon(t) = y(t) - \hat{y}(t|t-1)$ [Innovation or Residual]

$\hat{x}(t|t) = \hat{x}(t|t-1) + K(t)\epsilon(t)$ [Correction] (Equation 15)

where K(t) is the gain of the processor, which must be calculated from the underlying process statistics. Here Applicants have discretized time and measured it in units of the time step, so the time at the step before t is t−1.

For the cantilever array problem, Applicants must convert the physical relations, (2-12), into the state-space form above. Applicants chose to solve the differential equation and incorporate the resulting relations into the measurement (cantilever sensor) model. For the state, Applicants modeled the free energy as a piecewise constant function, converted it to discrete-time using the first difference approximation and excited it with zero-mean, white Gaussian (process) noise creating a random walk model for this parameter. Therefore, Applicants start with defining the state vector as $x := \Delta G$ and the deflection measurement $y := \Delta z$; then Applicants obtain the following relations. From (14), the surface concentration relation becomes simply $x(t) = \Delta x(t-1)$ [Process Model] (Equation 16)

The measurement model is more complicated. Applicants must first solve for the physical variables to obtain the generic form of (11); therefore, Applicants have from (2-12) that $y_i(t) = \Delta z_i^c(t) + \Delta z^T(t)$ [Measurement Model] (Equation 17)

where $\Delta z_i^c(t)$ is the chemically-induced deflection, different for different cantilevers. $\Delta z^T(t)$ thermal deflection, assumed to be the same for all cantilevers. In addition to accounting for the adsorption-desorption kinetics, Applicants also developed an approximation, based on the stirred tank reactor, to estimate the target concentration as a function of time under continuous flow conditions. In the experiments presented in this communication the applied chemical signal was a step function, i.e., a constant concentration at was turned on at time, $t_{ON}$, and off at time $t_{OFF}$. The dynamic surface concentration, $v(t)$, has the following form:

$$\Gamma(t)/\Gamma_{max} = 0, \quad t < t_{ON}$$

$$\Gamma(t)/\Gamma_{max} = \left(\frac{c(t)}{c(t) + k_a/k_d}\right)\{1 - \exp[-(k_a c(t) + k_d)(t - t_{ON})]\}, \quad t_{ON} \leq t \leq t_{OFF}$$

$$\Gamma(t)/\Gamma_{max} = \sqrt{\frac{1}{2k_d(t - t_{OFF})}}, \quad t > t_{OFF}$$

(Equation 18)

As described above, the differential surface stress on the cantilever is a function of the surface concentration and free energy $\Delta\sigma(t) = \Gamma(t)\Delta G(t) = \Gamma(t)x(t)$ (Equation 19)

The deflection of the $i^{th}$-lever is weighted by the Stoney equation with a specific value of $\beta$, from (5):

$\Delta z_i^c(t) = \beta_i \Delta\sigma(t)$, for $\beta_i := 3l^2(1-v)/(E_i \delta_i^2)$ (Equation 20)

where $\beta_i$ is the $i^{th}$-Stoney coefficient with cantilever modulus, $E_i$, with lever length and thickness, $l$ and $\delta_i$, respectively, and $v$ is Poisson's ratio for silicon. Here Applicants allow different values of $\beta$ for the different cantilevers to account for the well-known variations in cantilever properties, something that has been investigated extensively in the context of AFM cantilever spring constants. In principle, variations in either E or $\delta$ could cause appreciable variations in $\beta$; in practice, the variation of the Young's modulus of silicon is much less than the variation of $\delta^2$. Fortunately, it is the same combination (E $\delta^2$) that enters both $\beta$ and the leading term of $k_1$, so a single fitting parameter suffices to account for variations in both. In practice Applicants have taken this parameter to be $E_i$. Thus, Applicants obtain the measurement equation at the $i^{th}$-cantilever as $y_i(t) = \beta_i \Gamma(t)x(t) + \Delta z^T(t)$ (Equation 21)

Finally, assuming that both noise sources are Gaussian random processes (as before), then the result is a time-varying Gauss-Markov (not approximate due to linearity) multi-channel cantilever model defined by $x(t) = x(t-1) + w(t-1)$ $y_i(t) = \beta_i \Gamma(t)x(t) + \Delta z^T(t) + v_i(t)$ (Equation 22)

for $w \sim N(0, R_{ww})$; $v \sim N(0, R_{vv})$. As before, Applicants can develop the model-based processor based on this Gauss-Markov model. First, Applicants define the signal enhancement problem in terms of the cantilever models as:

Given a set of noisy $N_y$-vector displacement measurements, $\{y(t)\}$ with known $N_u$-vector inputs, $\{u(t)\}$ and parameters, $\{\theta_k\}$ specified by the Gauss-Markov model of (14), Find the best (minimum error variance) estimate of the displacement and $N_x$-vector surface concentrations, $\hat{y}(t|t-1)$, $\hat{x}(t|t)$, respectively.

The model-based algorithm to solve this problem using the specified models is:

Cantilever Array Model-Based Processor Algorithm $\hat{x}(t|t-1) = \hat{x}(t-1|t-1)$ [Surface Concentration Prediction]

$\hat{y}_i(t|t-1) = \beta_i \Gamma(t)\hat{x}(t|t-1) + \hat{\tau}(t)$ [Displacement Prediction]

$\epsilon_i(t) = y_i(t) - \hat{y}_i(t|t-1)$ [Innovation or Residual]

$\hat{x}(t|t-1) = \hat{x}(t-1|t-1) + k(t)\epsilon(t)$ [Surface Concentration Correction] (Equation 23)

This completes the development of the MBP algorithm for cantilever sensor arrays. Note that once this framework is developed, it is straightforward to define other problems of high interest (e.g., detection problems).

Figure 3:
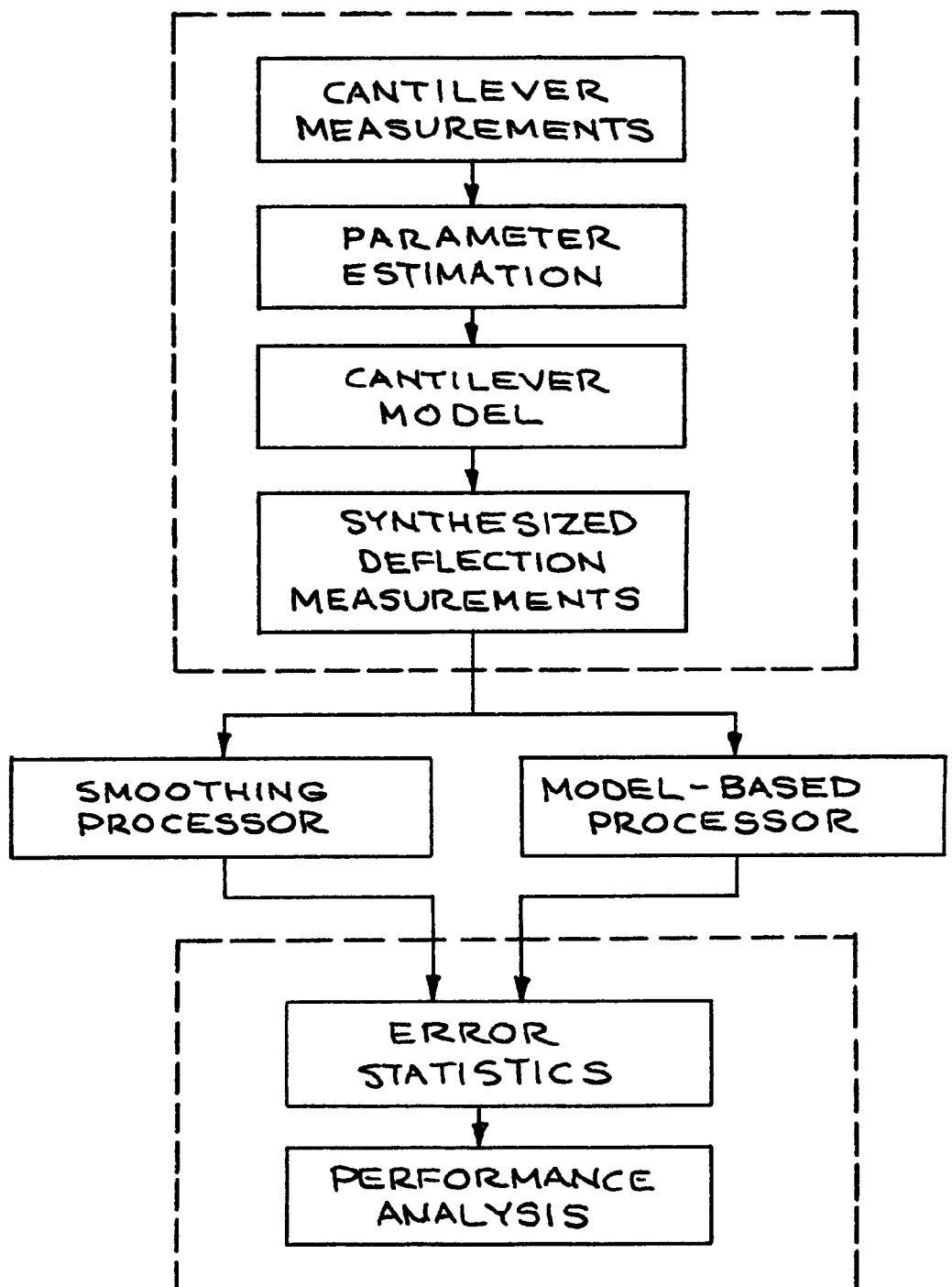
FIG. 3 illustrates a Model-Based Processor Performance Evaluation: Simulation, Processing and Analysis.
Figure 4A:
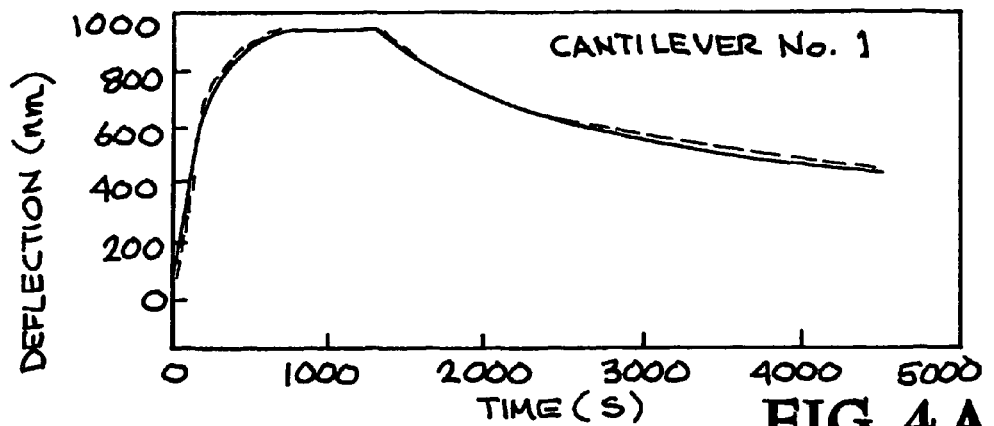
FIG. 4 shows Parameter Estimator Results: Fitted response (solid line) compared to the average experimentally-measured deflection (dotted line).
Figure 4B:
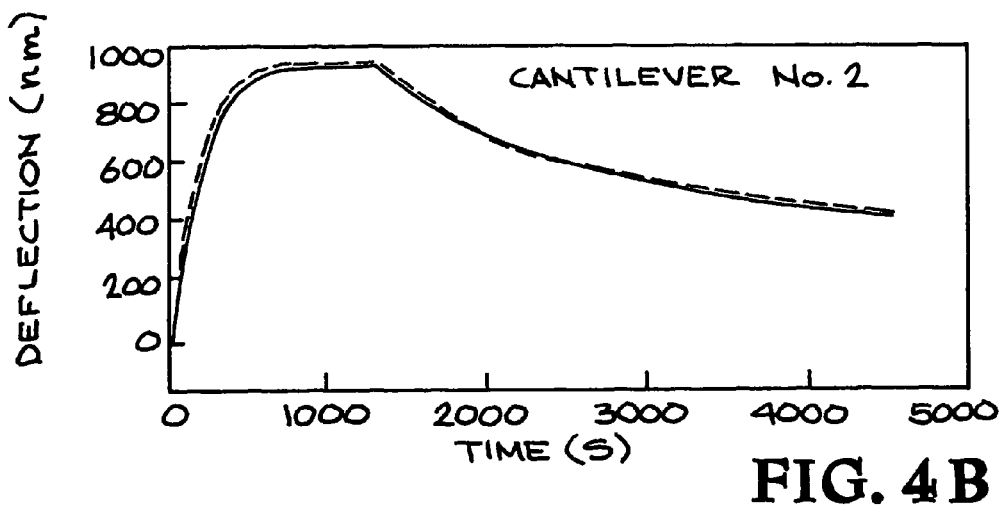
Figure 4C:
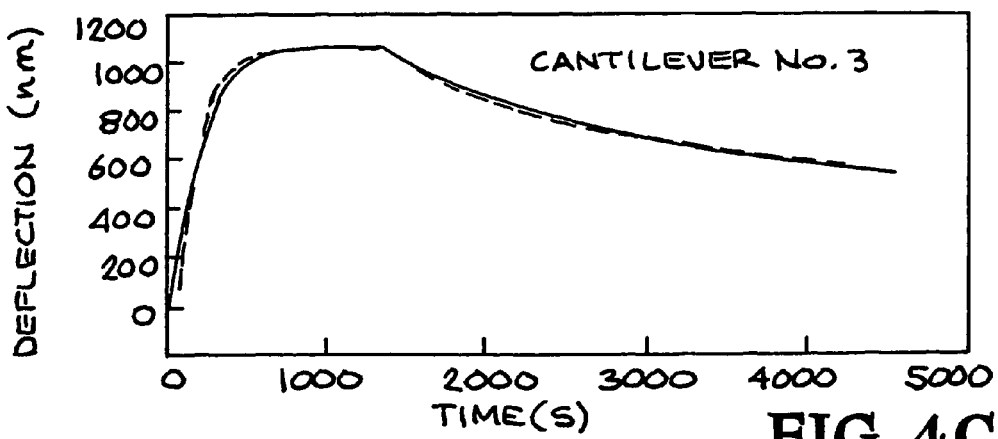
Figure 4D:
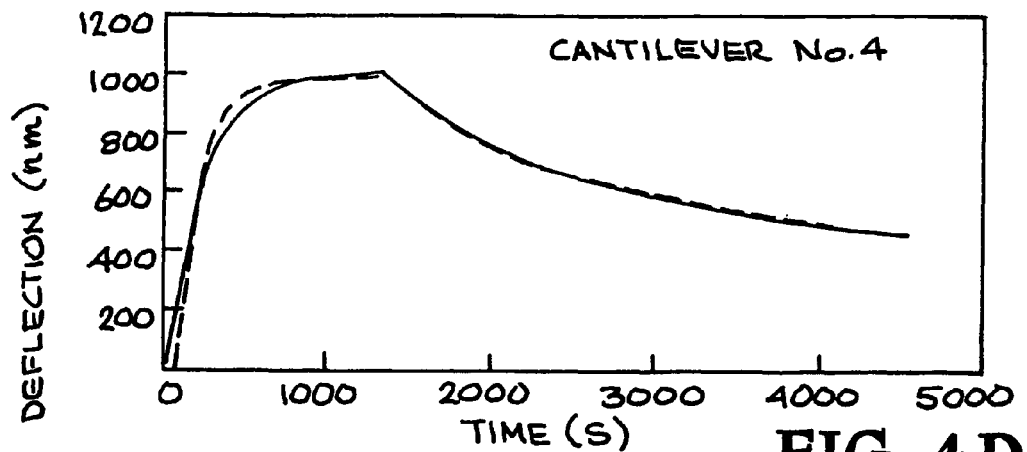
Figure 4E:
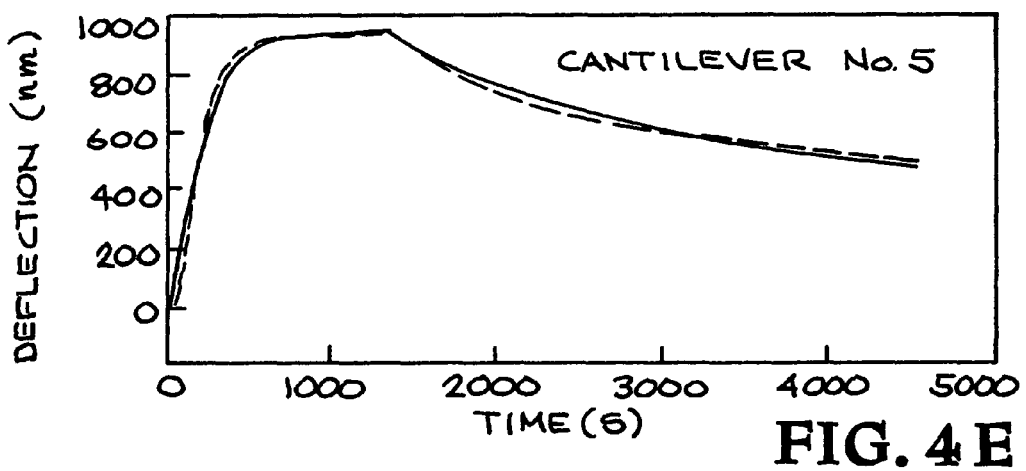
Figure 4F:
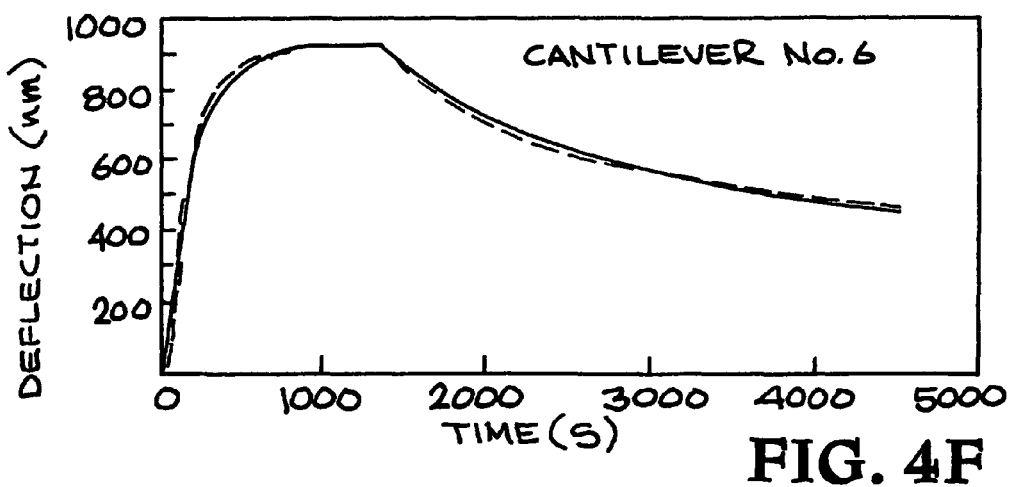
Figure 5A:
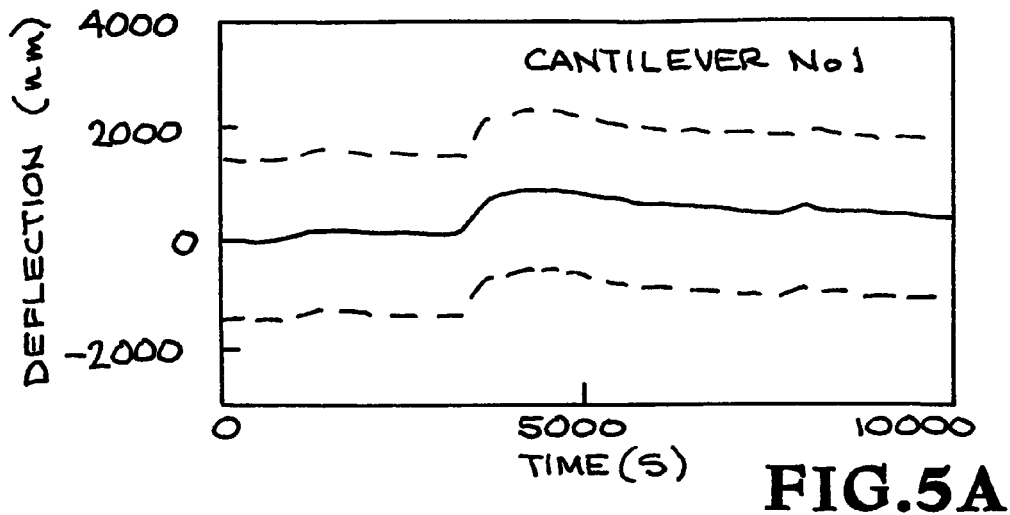
FIG. 5 illustrates Noisy Cantilever Deflection Measurement Gauss Markov Simulation (−20 dB SNR).
Figure 5B:
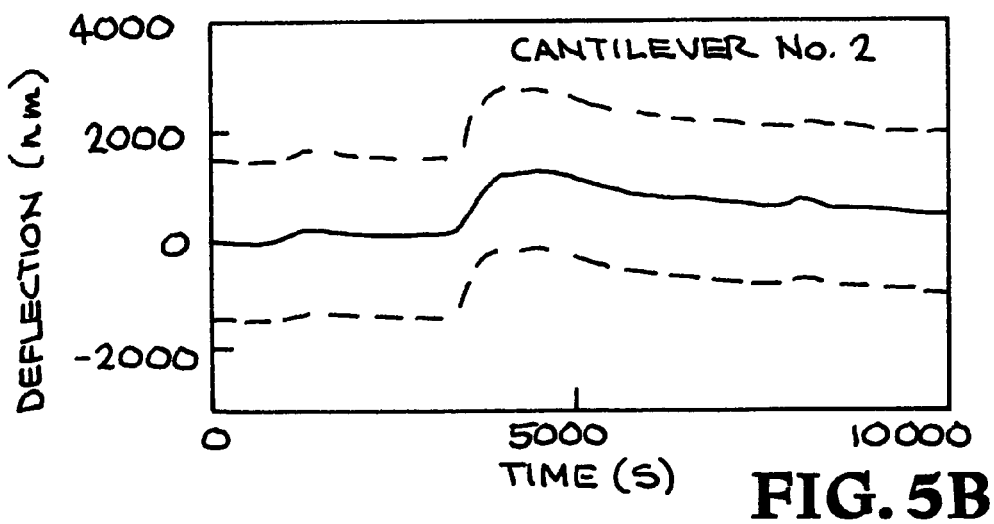
Figure 5C:
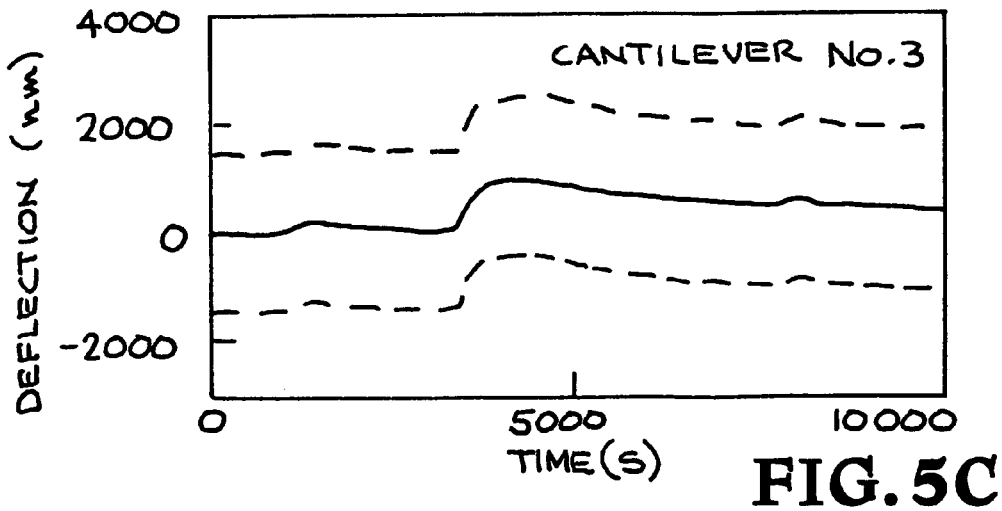
Figure 5D:
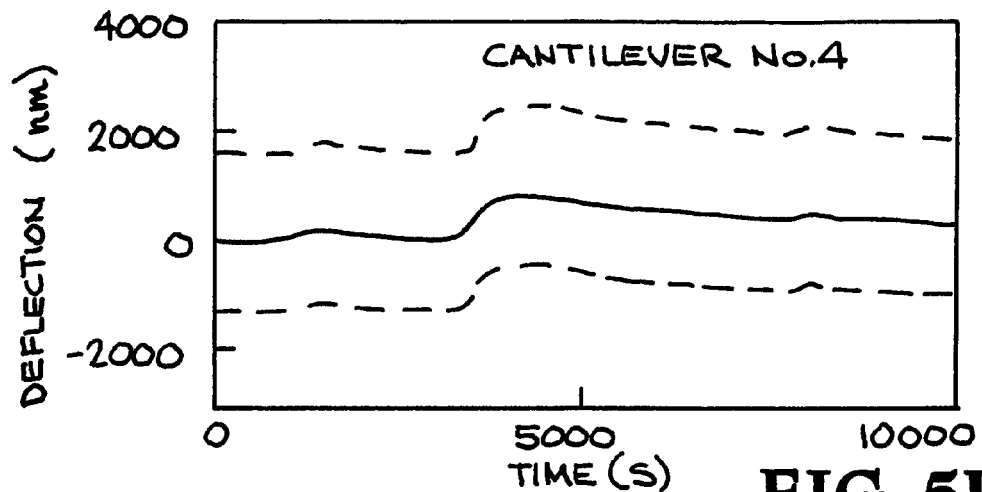
Figure 5E:
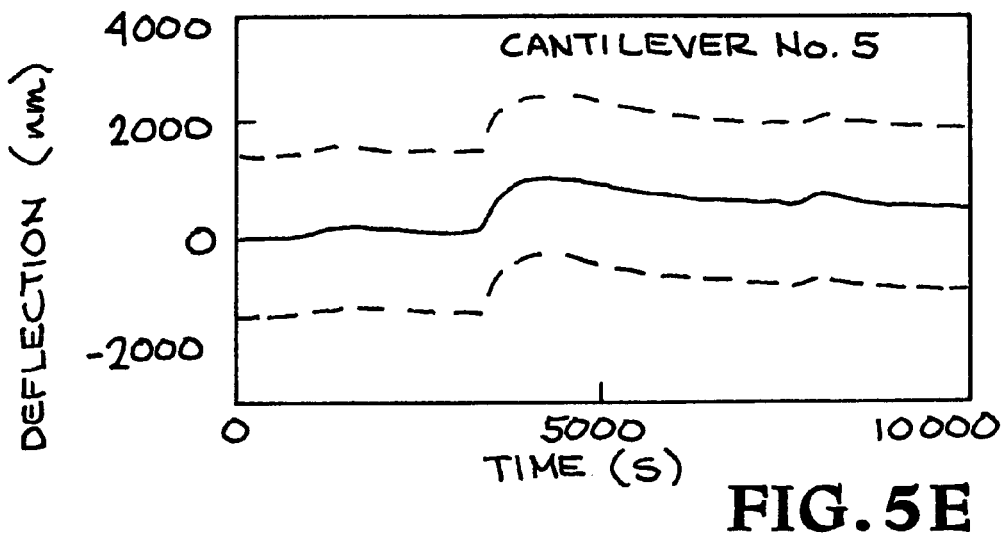
Figure 5F:
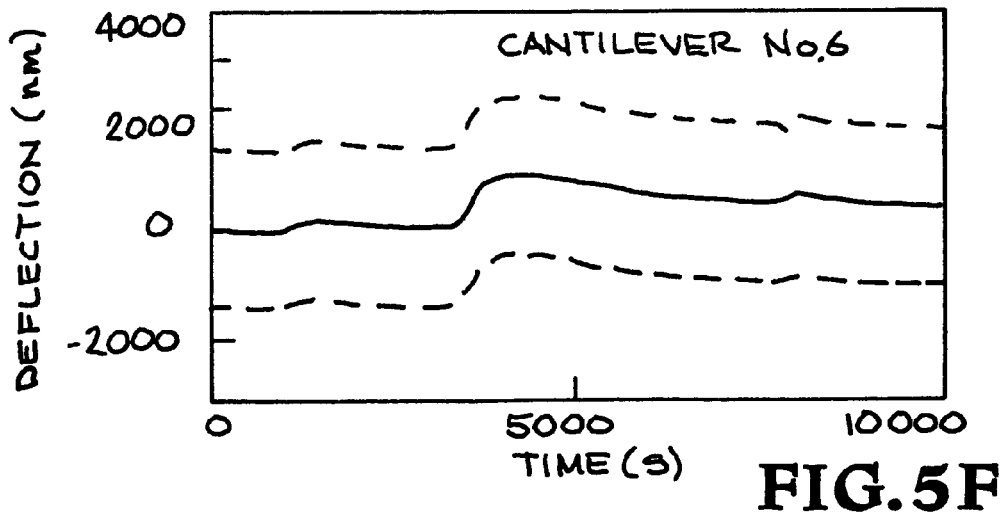
Figure 6A:
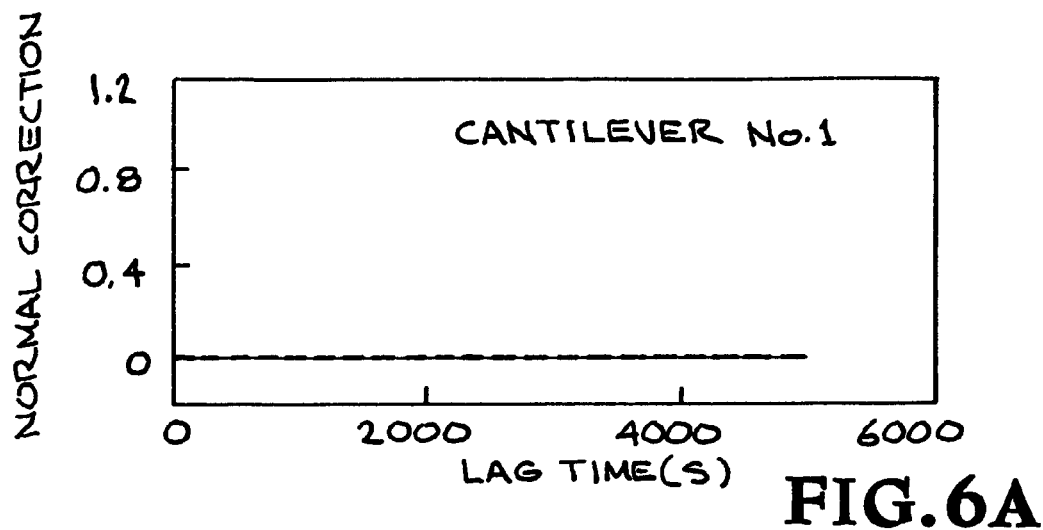
FIG. 6 shows Optimality Tests: Cantilever Array Zero-Mean/Whiteness and Weighted-Sum Squared Residual (WSSR) Statistic.
Figure 6B:
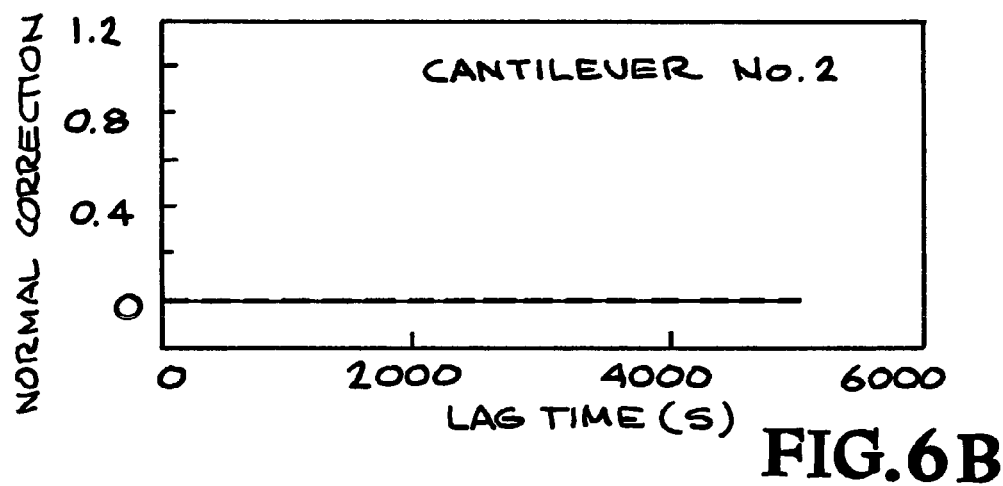
Figure 6C:
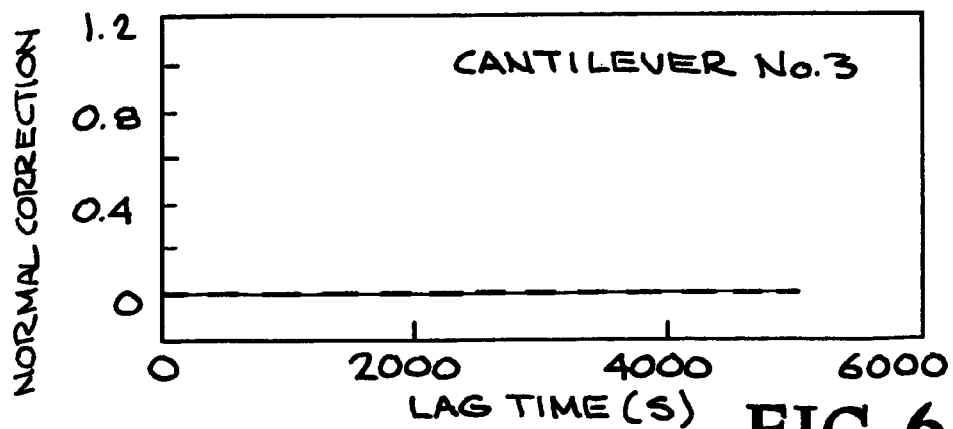
Figure 6D:
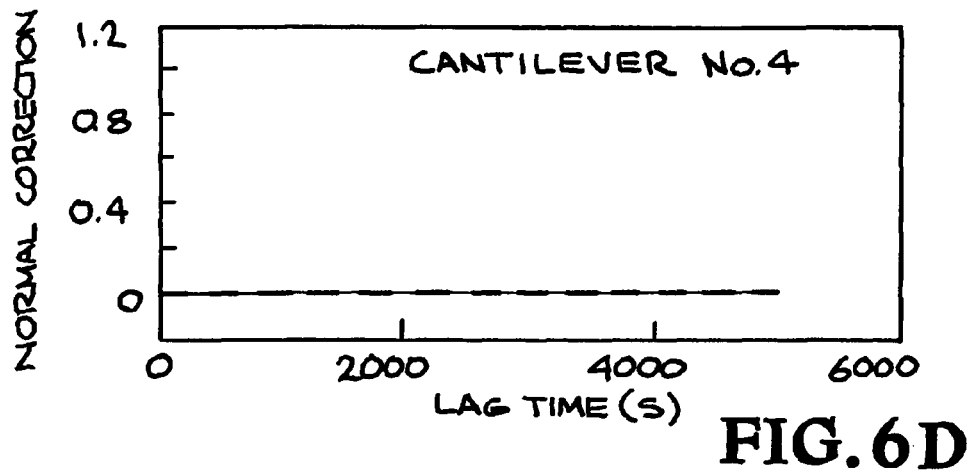
Figure 6E:
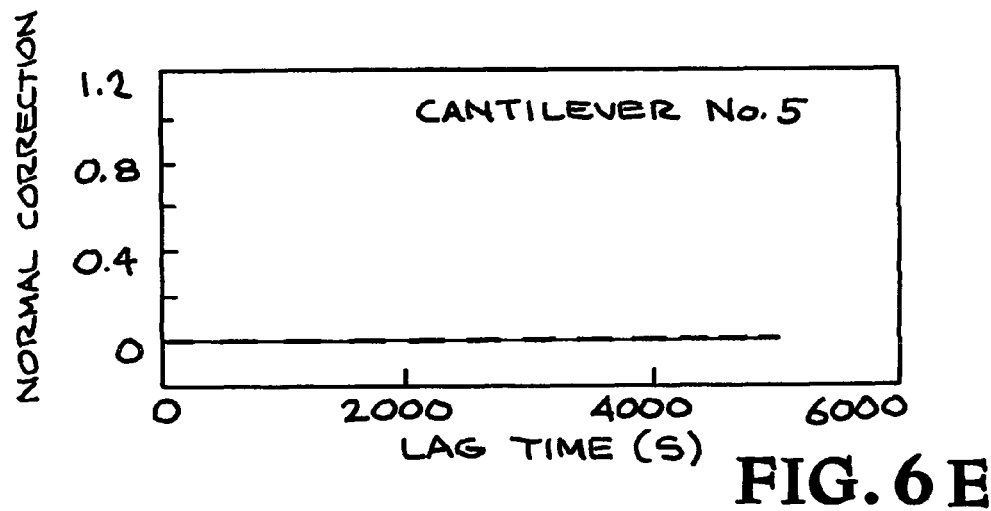
Figure 6F:
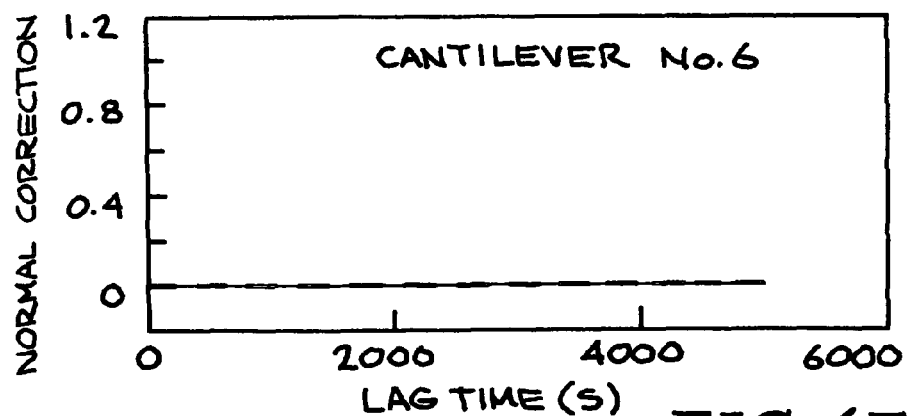
Figure 6G:
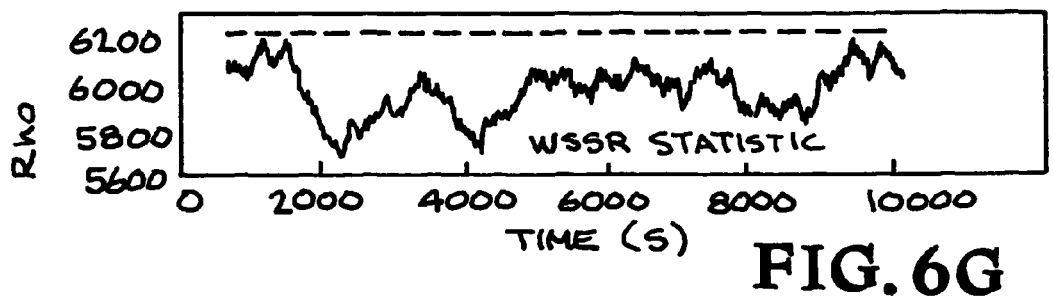
Figure 7A:
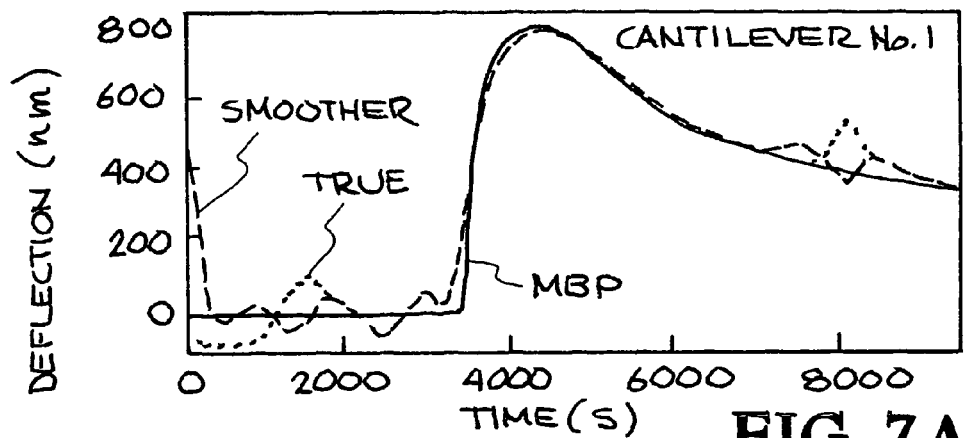
FIG. 7 shows MBP and Smoother Enhancement of the Noisy (−20 dB SNR) Synthesized Deflection Measurements: True Measured Deflection (with temperature-induced signals), Smoothed and MBP Estimates.
Figure 7B:
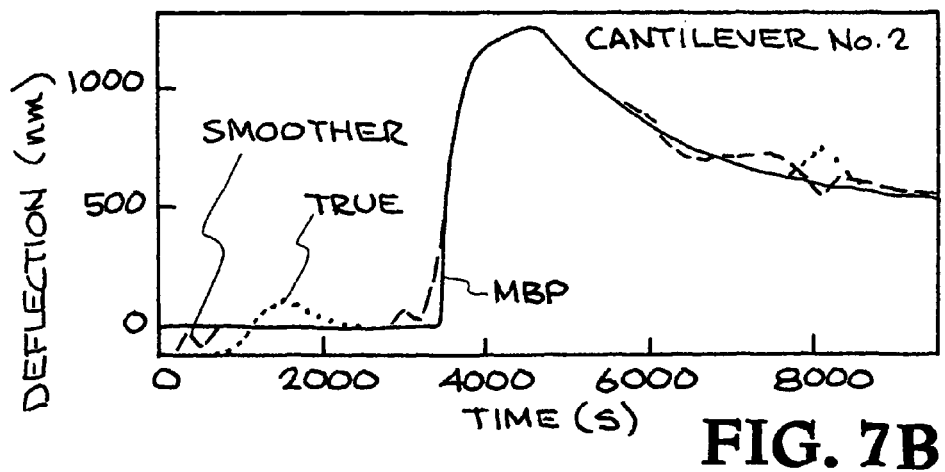
Figure 7C:
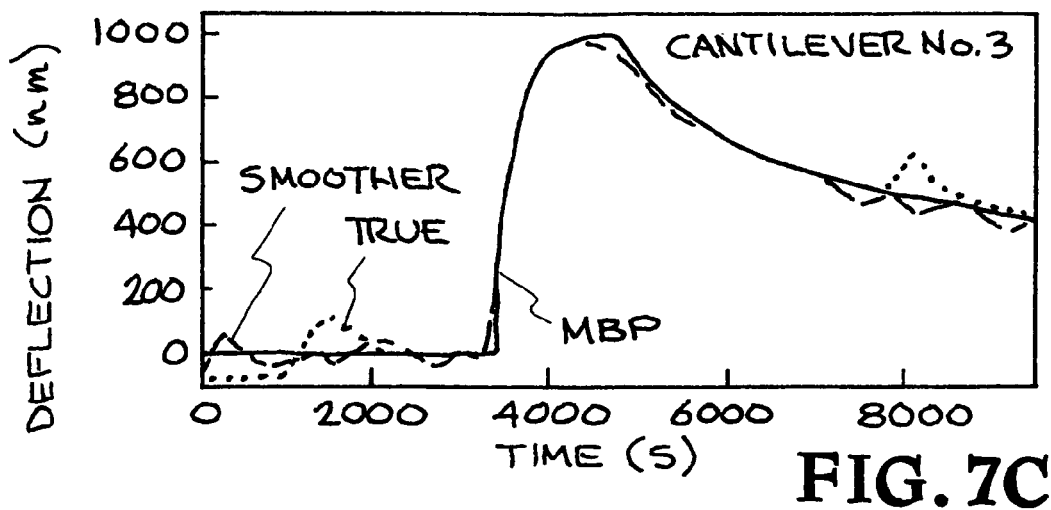
Figure 7D:
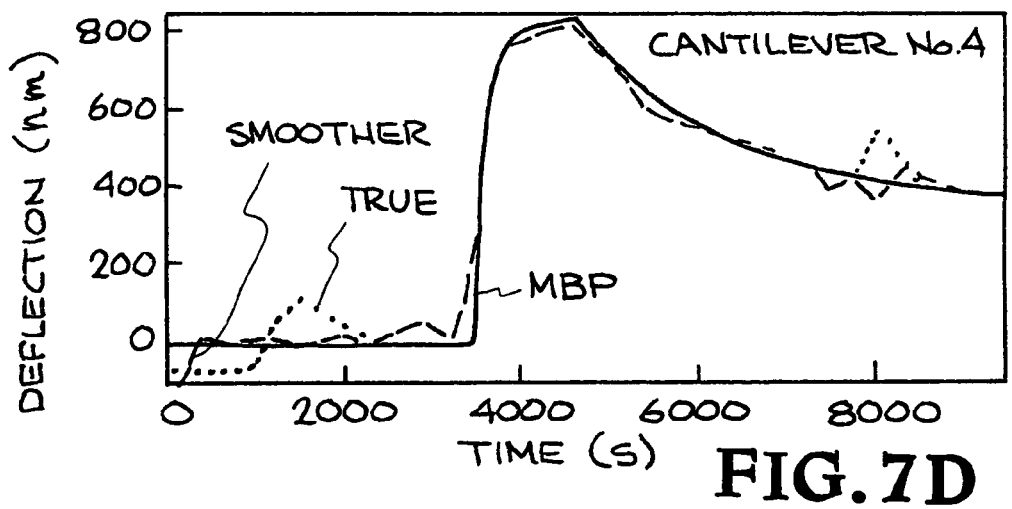
Figure 7E:
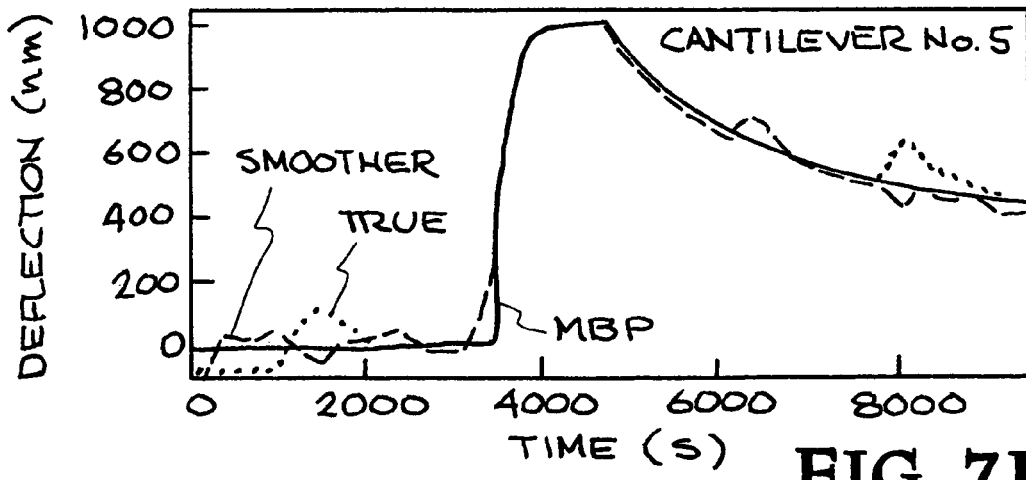
Figure 7F:
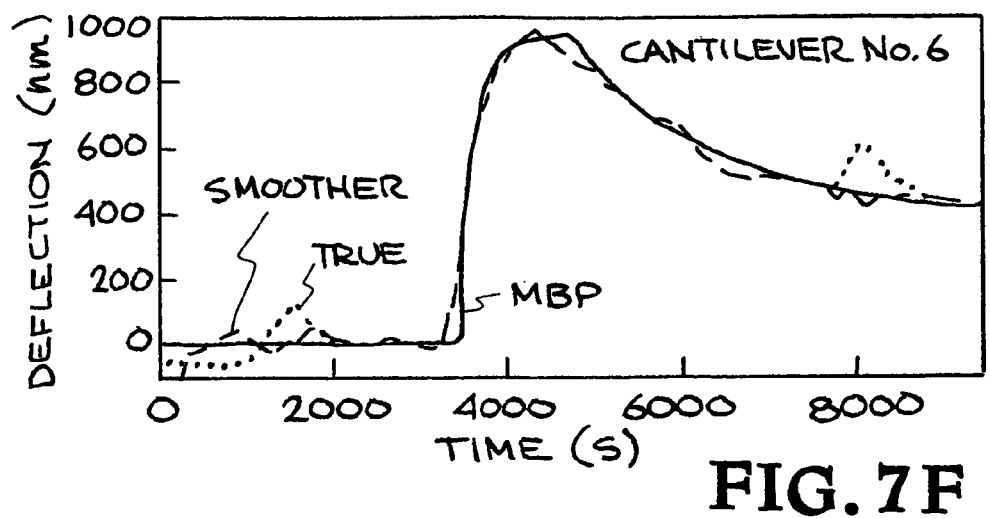

Model-based processor performance evaluation—Applicants will discuss the performance of the model-based processor (MBP) for signal enhancement of an L-element cantilever sensor array. The basic approach Applicants take for MBP performance evaluation is illustrated in FIG. 3. After obtaining the average parameters by performing the parameter estimation, a Gauss-Markov simulation was designed to generate synthesized cantilever deflection measurements using the model discussed in the previous section. Once synthesized at a particular signal-to-noise ratio (SNR), the processors were applied to the data and their performance analyzed based on the "truth" deflections generated by a noise-free simulation. Metrics are applied to evaluate and compare performance. Applicants discuss the various steps in this procedure.

Parameter Estimation. The basic approach Applicants use is to first "parameterize" the cantilever array model by performing parameter estimation (nonlinear least squares method) on the raw deflection measurements to extract the critical absorption, desorption and maximum concentration, that is, $\theta_i = \{k_a(i), k_d(i), \Gamma_{max}(i)\}$; i=1, ..., L. The parameter estimator Applicants employed was a nonlinear least-squares criterion using the Nelder-Meade polytope search algorithm. This algorithm is based on minimizing $$\min_{\theta_i} J(\theta) = \sum_{t=1}^{N_t} \varepsilon_i^2(t; \theta) \text{ for } \varepsilon(t; \theta) := y_i(t) - \hat{y}_i(t; \theta), \quad \text{(Equation 24)}$$

where the estimated or filtered cantilever measurement at the $i^{th}$-lever is given by $$\hat{y}_i(t;\theta) = \Delta z_i^c(t;\theta) + \Delta z^T(t) \quad \text{(Equation 25)}$$

Once these parameters are extracted from the data, they are averaged to give $\bar{\theta} = \{\bar{k}_a, \bar{k}_d, \bar{\Gamma}_{max}\}$. These are the parameters that are used in the Gauss-Markov simulation model.

Applicants tested the parameter estimator with raw experimental deflection data (FIG. 2) to determine the appropriate physical parameters for each lever on a single chip. Modeling results are shown in FIG. 4 where Applicants see the "fitted" deflection responses compared to the measured. It is clear that the extracted parameters reasonably fit the filtered cantilever response of (25). Next Applicants investigate the development of the simulator.

Gauss-Markov Model Simulation. For Applicants problem Applicants chose to use $\Delta G(t)$ as an unknown but constant parameter $$\left(\frac{d\Delta G(t)}{dt} = 0\right)$$

and the nonlinear deflection and known temperature measurement; that is, defining $$\Delta G(t) = \Delta G(t-1) + w(t-1) \quad \text{(Equation 26)}$$

with cantilever array measurement $$y_i(t) = \beta_i \Gamma(t) \Delta G(t) + \Delta z^T(t) + v_i(t) \quad \text{(Equation 27)}$$

where $\Delta G(t)$ is the free energy at the surface, and $w, v_i$ are the additive, zero-mean, Gaussian noise processes with covariances, $R_{ww}$ and $R_{vv} \in R^{L \times L}$ with diagonals, $\sigma_v^2(i)$; i=1, ..., L. Applicants assume that the measurement uncertainty is uncorrelated producing the diagonal matrix. Each of the cantilevers has a different value of $\beta_i$ creating a set of Stoney coefficients, $\beta \rightarrow \beta_i$, one representing each of the individual lever properties. A typical set of cantilever simulation data is shown in FIG. 5 where Applicants used a −20 dB SNR defined by:

$$SNR_i = \frac{\sigma_{\Delta z, true}^2(i)}{\sigma_v^2(i)}; \quad \text{(Equation 28)}$$

$$i = 1, \cdots, L$$

where $\Delta z_{true}$ is the "true" deflection available from the Gauss-Markov simulation and $\sigma^2_{\Delta z, true}$ is its variance. Once the noisy deflection measurements are synthesized, then the processors are applied to extract the "true" deflections. Applicants chose to evaluate two methods: smoothing processor and model-based processor. The smoothing processor is simply a running window average that is equivalent to a low-pass filtering operation. This smoothing is an example of a typical approach taken by scientists in this field. The MBP is the "optimal" (approximately) solution to this problem. Applicants used SSPACK_PC, a commercial model-based signal processing package in MATLAB, to perform these calculations. Table 1 gives the values of parameters for the cantilever used in the calculations.

TABLE I

Parameters Used in Model-based Processor

| Parameter | Value |
| --- | --- |
| E, Young's modulus for Si cantilever, Pa | $1.5 \times 10^{11}$ |
| v, Poisson's ratio for Si cantilever, unitless | 0.23 |
| l, cantilever length, μm | 500 |
| W, cantilever width, μm | 100 |
| δ, cantilever thickness, μm | 1 |

MBP application to single channel cantilever data—The MBP was developed using the cantilever measurement model of (29) with the average parameter estimates of Table II. Concerning the values given in Table II, it is helpful to review results obtained in related chemical systems. For example, $k_a$ is $1.3 \times 10^{-2}$ s$^{-1}$ for $CH_3$ $(CH_2)_{15}$ S/Au ($10^{-3}$ M) in ethanol, relatively constant between concentrations of $10^{-3}$ and $10^{-5}$M; Applicants average value of $4.6 \times 10^{-3}$ s$^{-1}$ for $k_a$ for 2-mercaptoethanol, $C_2H_6OS$, ($1.4 \times 10^{-2}$ M) in water is smaller, possibly because of different kinetic mechanisms that are active for this smaller molecule at higher concentrations, or because of solvent differences. Unlike the longer $CH_3$ $(CH_2)_{15}$ S, for example, 2-mercaptoethanol does not form well-ordered monolayers on Au. For 20-base pair thiolated DNA on Au in buffer, $k_d$ is $4.7 \times 10^{-3}$ s$^{-1}$, and $\bullet_{max} = 1.3 \times 10^{13}$ molecule/cm$^2$. Applicants value of $4.8 \times 10^{-4}$ s$^{-1}$ for $k_d$ is smaller, again possibly because of molecular size or solvent differences. $\bullet_{max}$ for $C_2H_6OS$ is larger ($1.3 \times 10^{15}$ molecule/cm$^2$), likely because the much smaller $C_2H_6OS$ is better able to concentrate on the Au surface.

TABLE II

Cantilever Parameter Estimation for 2-Mercaptotethanol $C_2H_6OS$ ($1.4 \times 10^{-2}$ M) in Water

| CANTILEVER | $K_a(10^{-3})(S^{-1})$ | $K_d(10^{-3})(S^{-1})$ | $\Gamma_{max}(10^{13}$ molecules cm$^2$) |
| --- | --- | --- | --- |
| 1 | 4.66 | 5.14 | 1.27 |
| 2 | 4.61 | 5.58 | 1.32 |
| 3 | 4.47 | 4.36 | 1.35 |
| 4 | 4.61 | 4.35 | 1.26 |
| 5 | 4.34 | 4.41 | 1.21 |
| 6 | 4.79 | 4.76 | 1.16 |
| AVERAGE | 4.6 | 4.8 | 1.3 |

Applicants will discuss the application of the MBP to simulated cantilever array measurement data at a variety of signal-to-noise ratios. Applicants first show the results of the MBP design for the −20 dB SNR case, then summarize the results at a variety of signal-to-noise ratios to evaluate its overall performance. The MBP design is based not only on the average parameter estimates (see Table II), but also using a smoothed temperature data estimate, $\Delta \hat{z}^T(t)$, to be more realistic in performance evaluation. Applicants expect this processor to provide an outstanding performance, once tuned. In fact, the results of applying it to the −20 dB data indicate an approximate optimal performance, since the underlying prediction errors or innovations associated with each lever are statistically zero-mean (mean less than bound) and white (less than 5% of the points outside the bound) as shown in FIG. 6 and Table III. To pass in Table III, simulated data must be zero-mean and white. Table III also shows the aggregated weighted-sum squared residual (WSSR) statistic indicating optimal performance. The results of processing the −20 dB SNR deflection data are shown in FIG. 7 for each lever. The results are shown by comparing the "true" (synthesized) deflection compared to the smoothed and MBP estimates. It is clear from the figure that the MBP performs extremely well.

TABLE III

MBP Optimality Zero-Mean/Whiteness Test Results

| Cantilever | Mean | Bound | Whiteness (% out) | Pass/Fail |
|---|---|---|---|---|
| No. 1 | 7.64 | 16.7 | 4.25 | p |
| No. 2 | 7.81 | 16.6 | 4.48 | p |
| No. 3 | 11.6 | 16.9 | 4.39 | p |
| No. 4 | 8.98 | 16.5 | 3.59 | p |
| No. 5 | 1.93 | 16.8 | 4.51 | p |
| No. 6 | 4.16 | 16.6 | 4.34 | p |

Next Applicants investigate the overall performance of both the standard smoother/averager and the MBP on synthesized data sets. In order to quantitatively evaluate the performance of the processors individually, Applicants calculate the residual deflection errors defined by $$\Delta \tilde{z}^c_i(t) := \Delta z^c_{true,i}(t) - \Delta \hat{z}^c_i(t) \quad \text{(Equation 29)}$$

where $\Delta z^c_{true,i}(t)$ is the true (noise free) deflection at the $i^{th}$-lever and $\Delta \hat{z}^c_i(t)$ is the filtered or estimated deflections as shown for the −20 dB case in FIG. 7. Once the error is estimated at each lever, its associated mean and variance can be calculated and used for further analysis. Applicants define the processor output gain as the final metric given by:

$$SNR_{out}(i) := \frac{\sigma^2_{\Delta z, true}(i)}{\sigma^2_{\Delta \tilde{z}, true}(i)};$$

$$i = 1, \cdots, L.$$
(Equation 30)

This ratio represents the enhancement provided by each processor. The smaller the residual error variance ($\sigma_{\Delta \tilde{z}}^2$), the higher the $SNR_{out}$, providing a reasonable metric. Averaging these statistics over the cantilever array gives a measure of overall processing gain.

TABLE IV

MBP/Smoother Performance Analysis

| | $SNR_{in}$(dB) | | | | | |
|---|---|---|---|---|---|---|
| Lever | 0 $SNR_o$ (Smt) | 0 $SNR_o$ (MBP) | −20 $SNR_o$ (Smt) | −20 $SNR_o$ (MBP) | −40 $SNR_o$ (Smt) | −40 $SNR_o$ (MBP) |
| No. 1 | 44.0 | 79.9 | 36.5 | 79.9 | 17.6 | 79.9 |
| No. 2 | 46.0 | 87.2 | 40.2 | 87.2 | 26.3 | 87.2 |
| No. 3 | 44.9 | 83.3 | 44.5 | 83.3 | 23.5 | 83.3 |
| No. 4 | 45.2 | 80.3 | 37.9 | 80.3 | 17.3 | 80.3 |
| No. 5 | 44.8 | 83.8 | 39.8 | 83.8 | 22.9 | 83.8 |
| No. 6 | 45.9 | 82.4 | 40.0 | 82.4 | 24.0 | 82.4 |
| AVG | 45.1 | 82.8 | 39.8 | 82.8 | 21.9 | 82.8 |
| Avg Gain | | +37.7 | | +43.0 | | +60.9 |

Applicants performed a set of simulations at 0, −20, −40 dB $SNR_{in}$ with the typical run outputs shown in the previous figures for the −20 dB case. The results for each run are summarized in Table IV. Here Applicants see that output SNR produced by both processors are respectable with a significant gain in enhancement; however, it is clear that the MBP consistently demonstrates superior performance with an overall average enhancement of 80 dB and enhancement gain over the Smoother of 38, 43 and 60 dB, respectively. The MBP is insensitive at these SNRs to the measurement noise variance changes yielding identical performance at each level. By contrast, the Smoother performance clearly deteriorates as the input SNR decreases. The MBP performance will also deteriorate with decreases in input SNR, but not at realistic experimental levels. This demonstrates outstanding performance for multi-channel cantilever arrays on these simulated data sets. Next Applicants apply the process to the measured array data.

Model-based processor application to multichannel cantilever data—Applicants developed MBP for two cases: (1) average deflection data and an averaged cantilever model; and (2) multi-channel deflection data. First Applicants averaged the six cantilever deflection data to obtain the complete deflection response over the entire array. Applicants next designed the MBP: Applicants first obtained the parameter estimates, then applied those parameters to the processor. Finally, Applicants developed the multi-channel processor using the same approach: estimating the individual cantilever parameters, taking their average and calculating the appropriate parameters for the multi-channel model. In both cases Applicants performed simulations first to develop the optimal MBP.

Figure 8A:
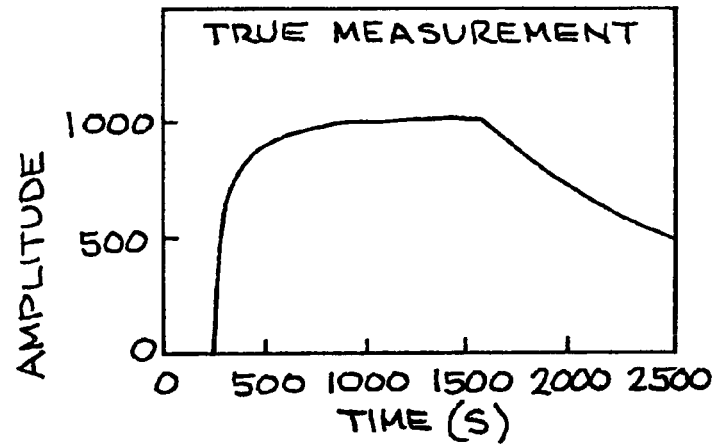
FIG. 8 shows MBP Design for Simulated Average Cantilever Data (0 dB SNR): (a) True measured signal. (b) Simulated Gauss-Markov deflection measurement with bounds. (c) Enhanced deflection (MBP output). (d) Optimality tests (zero-mean/whiteness) results.
Figure 8B:
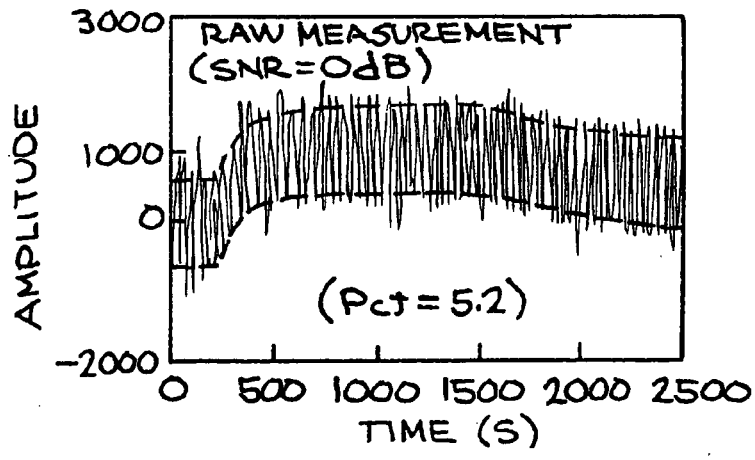
Figure 8C:
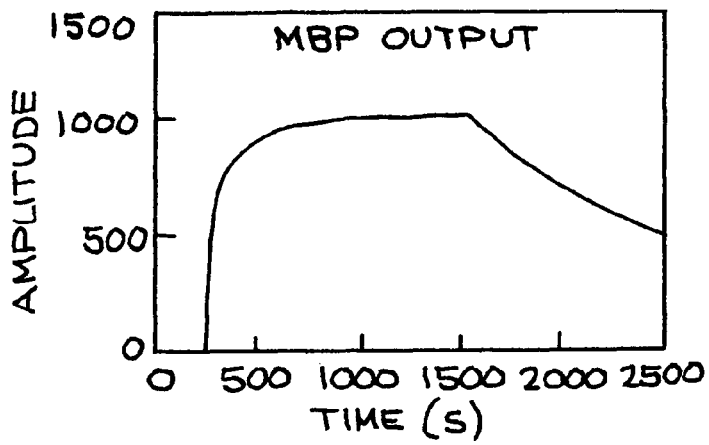
Figure 8D:
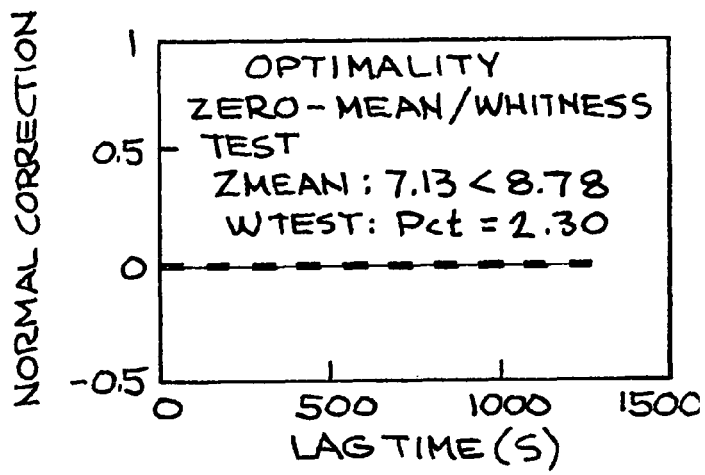

The average cantilever model was developed by performing the model-based parameter estimation obtaining the adsorption, desorption and free energy, then developing the corresponding Gauss-Markov simulation model and corresponding MBP. The raw and simulated data (0 dB) are shown in FIGS. 8a and 8b. It is clear that the measurement noise severely distorts the desired deflection signal. The enhanced MBP output (deflection) enhancement is shown in FIG. 8c along with the corresponding optimality tests in 8d, where it is apparent that the performance of the processor is indeed optimal: the corresponding innovations are zero-mean and white.

Figure 9A:
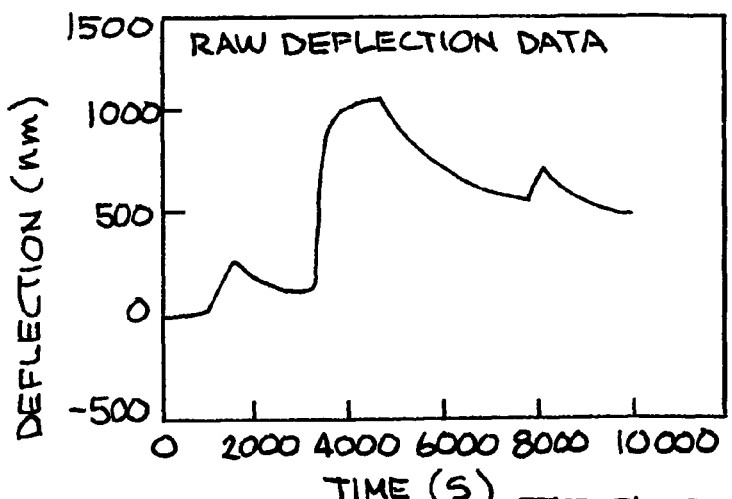
FIG. 9 shows Average Cantilever MBP Application to Measured Deflection Data. (a) Experimentally measured deflection data. (b) Measured temperature profile data. (c) Model-based parameter estimation fit and parameters. (d) Model-based enhancement including temperature.
Figure 9B:
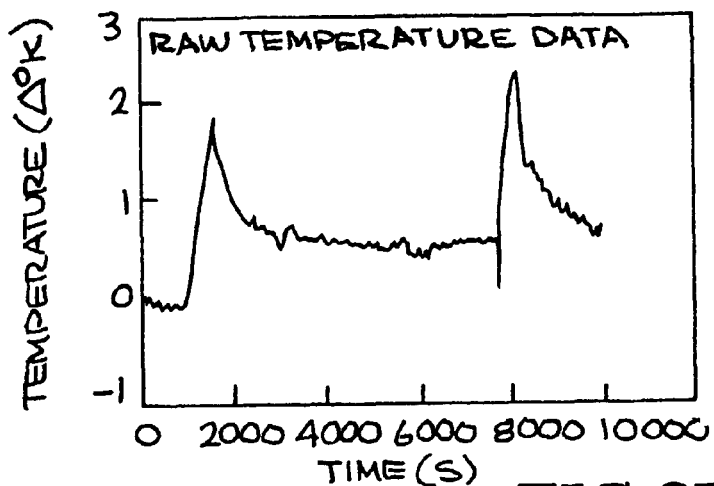
Figure 9C:
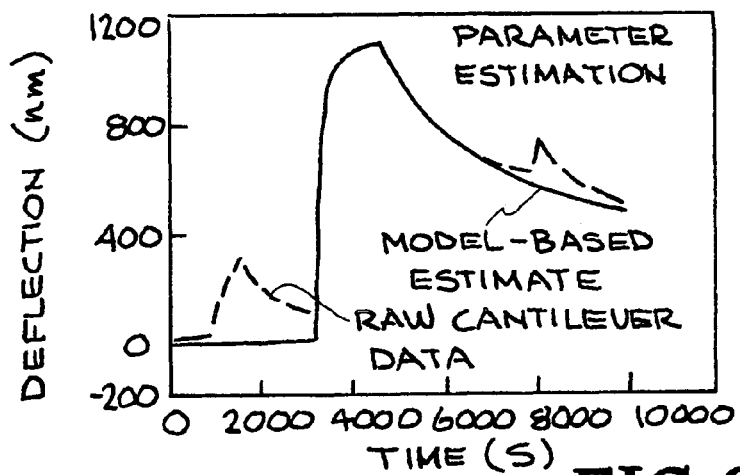
Figure 9D:
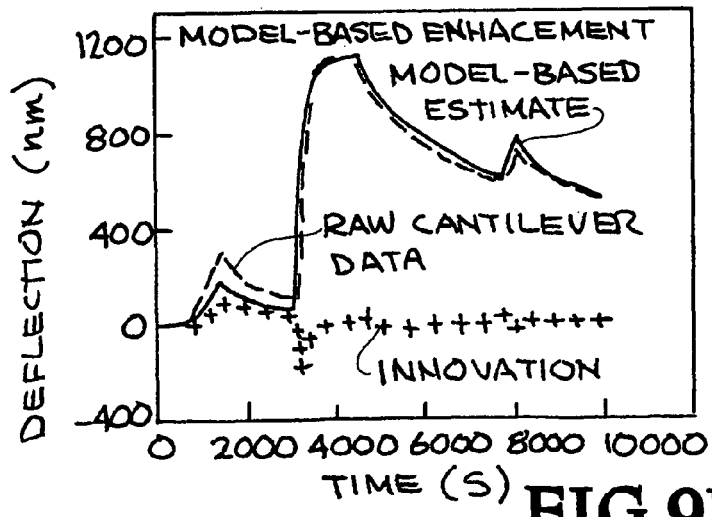
Figure 10A:
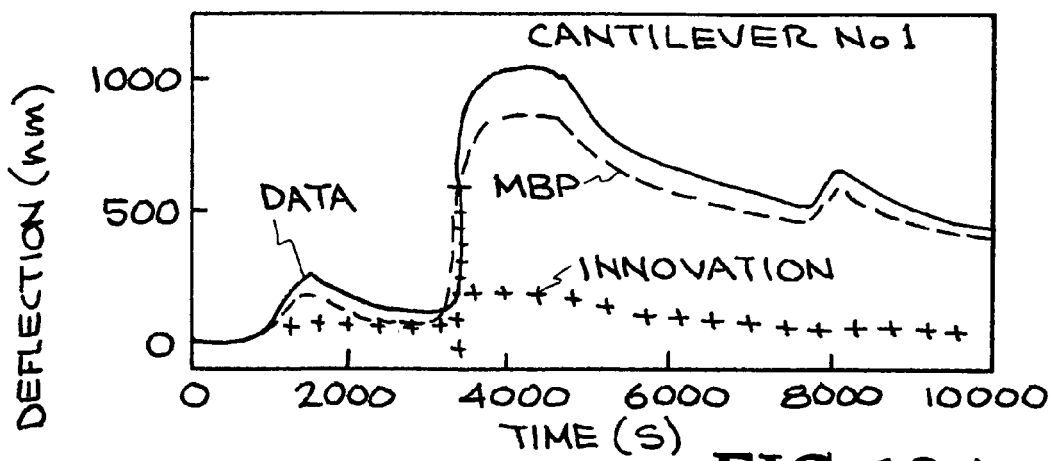
FIG. 10 shows MBP of Experimental Cantilever Array Data: Experimentally-measured signal (Data), Enhanced (MBP) and Residual (Innovation) results for each lever.
Figure 10B:
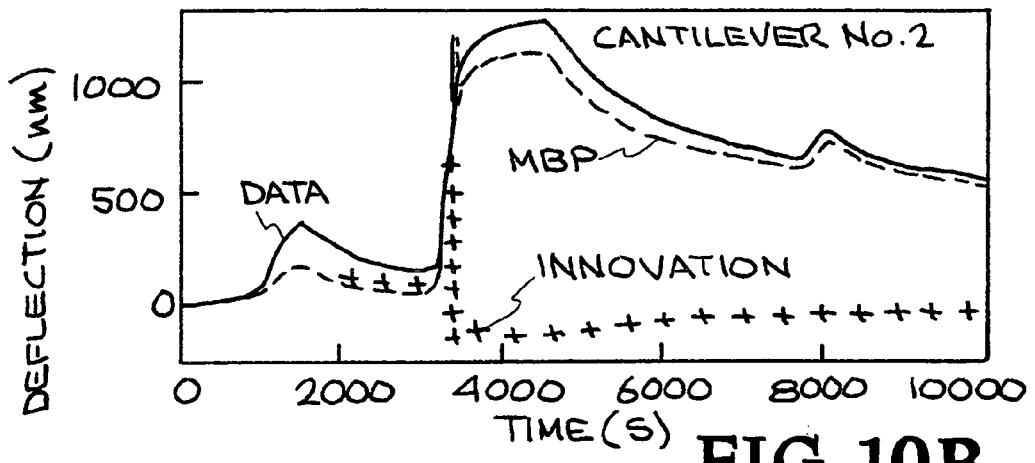
Figure 10C:
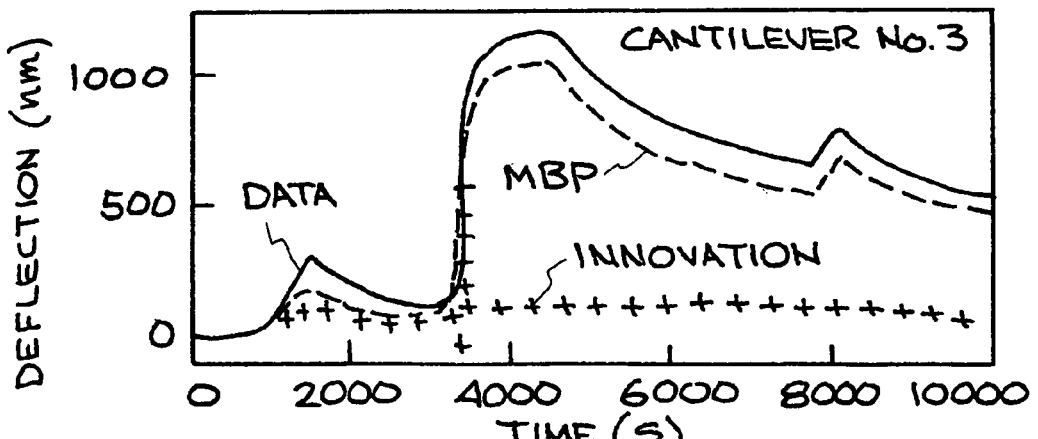
Figure 10D:
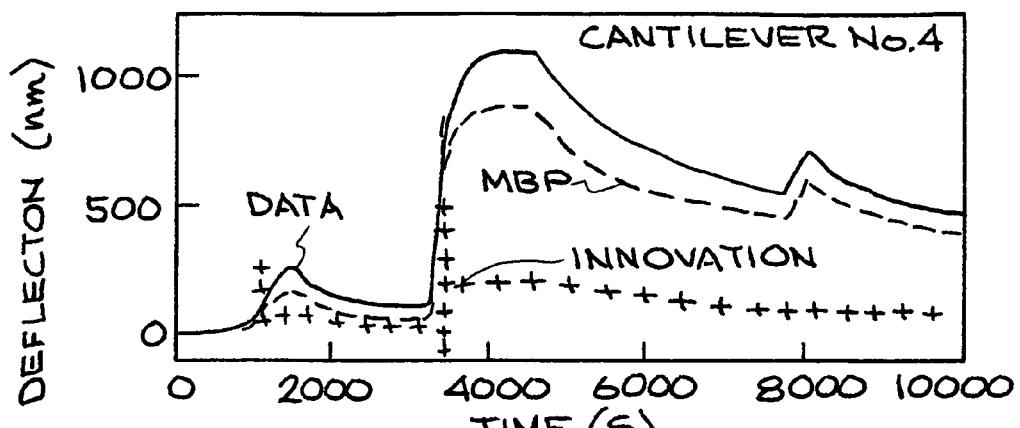
Figure 10E:
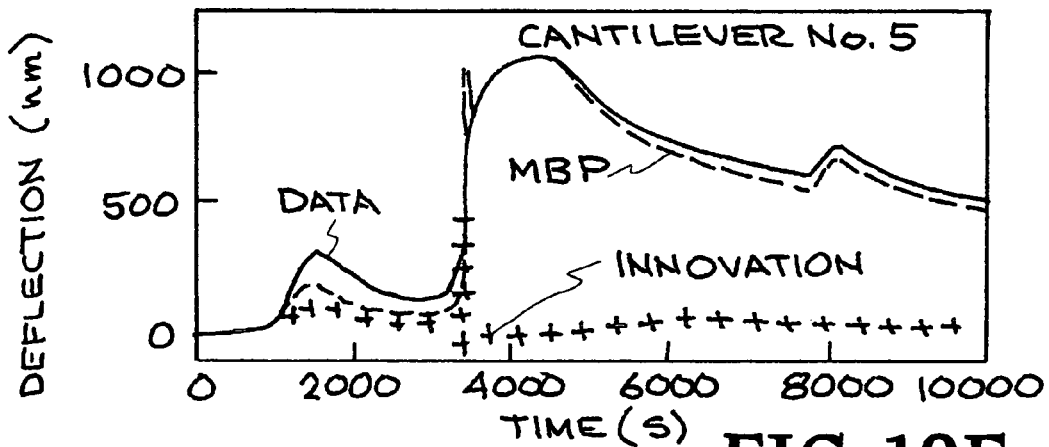
Figure 10F:
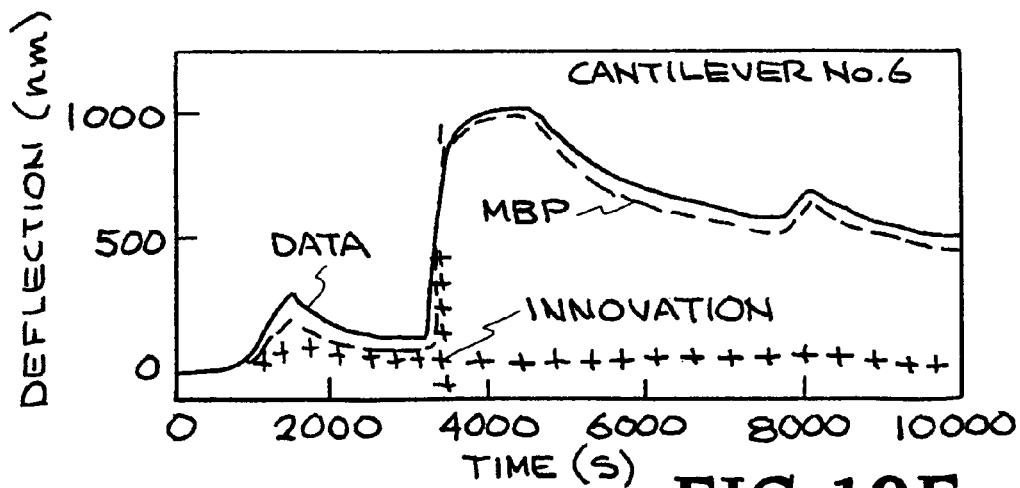

Next Applicants applied the MBP to the actual deflection and temperature profile data shown in FIGS. 9a and 9b after "tuning" the noise covariance parameters ($R_{vv}$) with the results shown in FIG. 9d. Here Applicants see that the MBP is capable of tracking the averaged cantilever deflection data quite well; however, the performance is suboptimal, since the innovation, although small, is not white. Generally, the MBP performance for this data is quite good.

Next Applicants developed the MBP for the multi-channel case using the same model-based approach: simulation and application. Applicants used the average model parameters developed over the entire cantilever array data set with the nonlinear least-squares model-based parameter estimator, then applied it to the raw cantilever data to investigate its performance. Applicants again used the MBP with the free energy as Applicants piecewise constant parameter (state) and the nonlinear cantilever array model with six elements. Applicants used the smoothed estimate of the temperature profile in Applicants estimator as in the synthesized data case. Applicants also used the estimated the Stoney coefficients and the average parameter estimates as before.

The measured cantilever data, MBP estimates and the corresponding errors or innovations are shown in FIG. 10. Since the innovations are not zero-mean and white, the processor is not optimal; however, the results are quite reasonable except for the systematic bias error (constant) in the estimate. The dynamics appear to be captured by the model especially well in cantilever five. The offset can be adjusted by selecting various combinations of elements in the $R_{vv}$ measurement noise covariance matrix, but this may be better suited to an adaptive implementation of the processor that will be pursued in future work. From the figure Applicants note that the dynamics of the individual levers (on-set and off-sets) are close to the expected dynamics.

Applicants have developed a successful model-based approach to the microcantilever array signal enhancement problem. Experimental data were obtained from a multi-cantilever detection system and quantitatively analyzed with mathematical tools from physical chemistry and solid state physics. Applicants incorporated the results of this analysis directly into the generic signal processing approach. A proof-of-concept solution was created to parameterize Applicants theoretical model, enabling us to test an average model. This model was then used to develop the MBP for enhancing noisy cantilever measurements. Applicants investigated data averaged over the array and the multi-channel cases.

Through simulations with additive Gaussian noise at SNR of 0, −20, and −40 dB, Applicants demonstrated the ability of the processor to extract the cantilever deflection response with a large improvement in signal gain (~80 dB). Applicants compared the performance of the processor to that of a "smoother" (averager) at several different signal-to-noise ratios, and the MBP demonstrated superior performance with an overall average processing gain of ~40-60 dB over the averager. Finally, Applicants applied the MBP to noisy, smoothed (averaged) cantilever data and demonstrated that the processor could perform quite well except for a bias error, which is easily corrected.

To demonstrate the full utility of the MBP for chemical sensing of low levels of signature chemicals, necessary next steps are (1) verify the physical models used in this study for a variety of solvents and target molecules (2) make use of control levers, and (3) extend the experimental library to include low concentrations of chemical targets of practical interest.

The present invention provides model based signal processing based on developing (signal processing type models) models of the process under investigation (chemistry), measurement or sensors (cantilever array) and noise/uncertainty (background noise, chemical noise, cantilever parameter uncertainty, etc.) and incorporating them into a signal processing scheme. The models developed are usually simplified or lumped versions of the process/measurement. Applicants developed simplified models of the system and process and incorporated them into a processor. When the actual sensor measurement (experiment) and gather data is made, since the MBP has this knowledge in the form of mathematical models, it is able to outperform other processors that do not. Advantages of the present invention include incorporating the process chemistry and flow across the cantilevers, using simple structural models to capture their bending and extract the parameter of most interest the deflection to obtain the information (species) being sought. The present invention provides a method of detecting chemical or biological agents utilizing deflection of a micromachined cantilever that represents the chemical or biological agent being detected employing a model-based signal processing scheme, comprising the steps of using process system model development including the thermodynamics, chemistry fluidics and statistical uncertainties associated with parameters and noise; using measurement system model development modeling the deflection of the micromachined cantilever producing a deflection model, along with its parametric uncertainties and noise; using noise models representing the inherent noise (instrumentation, background, etc.) of cantilever array measurement system; and incorporating said models into an optimal signal processing system able to extract both parameters of high interest as well of enhanced the noisy measurements, that is, significantly increasing the final signal-to-noise ratio.

The present invention has use with cantilever measuring and sensing systems. Cantilever measuring and sensing systems are used widely. Examples of cantilever measuring and sensing systems are described in U.S. Patent Application No. 2006/0075836 by Anis Zribi, Luana Emiliana Iorio, and Daniel Joseph Lewis for a pressure sensor and method of operation thereof; U.S. Patent Application No. 2006/0016270 by Roberto Cavenago and Massimo Gherlinzoni for a load sensor; and the article Measuring Contact Stress Inside Weapons Systems in the April 2006 issue of Science and Technology Review. U.S. Patent Application No. 2006/0075836 by Anis Zribi, Luana Emiliana Iorio, and Daniel Joseph Lewis for a pressure sensor and method of operation thereof; U.S. Patent Application No. 2006/0016270 by Roberto Cavenago and Massimo Gherlinzoni for a load sensor; and the article Measuring Contact Stress Inside Weapons Systems in the April 2006 issue of Science and Technology Review are incorporated herein by reference.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A method of detecting a chemical or biological agent utilizing deflection of a micromachined cantilever that represents the chemical or biological agent being detected employing a model-based signal processing scheme, consisting of the steps of:

providing a process system model including the thermodynamics, chemistry fluidics and statistical uncertainties associated with parameters and noise;

providing a measurement system model modeling the deflection of the micromachined cantilever producing a deflection model, along with its parametric uncertainties and noise;

providing noise models representing said noise of said measurement system model; and using said process system model, said measurement system model, and said noise models for detecting the chemical or biological-agent by incorporating said models into an optimal signal processing system able to extract both parameters of high interest as well of enhanced the noisy measurements, that is, significantly increasing the final signal-to-noise ratio.

* * * * *